(12) United States Patent
O'Rourke et al.

(10) Patent No.: US 8,791,079 B2
(45) Date of Patent: Jul. 29, 2014

(54) METHODS FOR TREATING HEART FAILURE BY INHIBITING THE MITOCHONDRIAL SODIUM-CALCIUM EXCHANGER (MNCE)

(75) Inventors: Brian O'Rourke, Sparks, MD (US); Ting Liu, Parkville, MD (US)

(73) Assignee: The Johns Hopkins University, Baltimore, MD (US)

( * ) Notice: Subject to any disclaimer, the term of this patent is extended or adjusted under 35 U.S.C. 154(b) by 68 days.

(21) Appl. No.: 13/255,593

(22) PCT Filed: Mar. 11, 2010

(86) PCT No.: PCT/US2010/026890
§ 371 (c)(1),
(2), (4) Date: Dec. 16, 2011

(87) PCT Pub. No.: WO2010/104998
PCT Pub. Date: Sep. 16, 2010

(65) Prior Publication Data
US 2012/0077763 A1    Mar. 29, 2012

Related U.S. Application Data

(60) Provisional application No. 61/159,148, filed on Mar. 11, 2009, provisional application No. 61/250,729, filed on Oct. 12, 2009.

(51) Int. Cl.
*A61K 31/7048* (2006.01)
*A61K 31/554* (2006.01)
*A61P 9/00* (2006.01)
*A61K 45/06* (2006.01)

(52) U.S. Cl.
CPC ........... *A61K 31/7048* (2013.01); *A61K 31/554* (2013.01); *A61K 45/06* (2013.01); *A61K 2300/00* (2013.01)
USPC ....................................... 514/26; 514/211.05

(58) Field of Classification Search
CPC . A61K 31/7048; A61K 31/554; A61K 45/06; A61K 2300/00
USPC .............................................. 514/26, 211.05
See application file for complete search history.

(56) References Cited

U.S. PATENT DOCUMENTS

| | | |
|---|---|---|
| 6,958,352 B2 | 10/2005 | Pei et al. |
| 2002/0082193 A1 | 6/2002 | Anderson et al. |
| 2004/0044049 A1 | 3/2004 | Pei et al. |
| 2004/0082521 A1 | 4/2004 | Singh |
| 2006/0004062 A1 | 1/2006 | Pei et al. |
| 2007/0054874 A1 | 3/2007 | Zeilig |
| 2008/0089947 A1 | 4/2008 | Knox et al. |

OTHER PUBLICATIONS

Glossary of medical education terms, Institute of International Medical Education. http://www.iime.org/glossary.htm Accessed in Mar. 2013.*
Dickstein et al. ESC Guidelines for the diagnosis and treatment of acute and chronic heart failure 2008. Eur Heart J 29:2386-2442, 2008.*
Kennedy et al. Suppression of Positive Inotropic and Toxic Effects of Cardiac Glycosides by Amiloride. Eur J Pharmacol 115:199-210, 1985.*
Maack et al. Elevated Cytosolic Na+ Decreases Mitochondrial Ca2+ Uptake During Excitation-Contraction Coupling and Impairs Energetic Adaptation in Cardiac Myocytes. Circ Res 99:172-182, 2006.*
Ting Liu et al., "Enhancing mitochondrial Ca2+ uptake in myocytes from failing hearts restores energy supply and demand matching", Circulation research, Jul. 3, 2008, 103, pp. 279-288.
Bongju Kim et al., "Mitochondrial Ca2+ flux through Na+/Ca2+ exchange", Ann. N. Y. Acad. Sci., 2007, 1099, pp. 507-511.
Koji Wakimoto et al., "Targeted disruption of Na+/Ca2+ exchanger gene leads to cardiomyocyte apoptosis and defects in heartbeat", the Journal of Biological Chemistry, Nov. 2000, 275(47), pp. 36991-36998.
T.E. Gunter et al., "Mitochondrial calcium transport: mechanisms and functions", Cell Calcium, 2000, 28(5), pp. 285-296.

* cited by examiner

*Primary Examiner* — Brandon Fetterolf
*Assistant Examiner* — Yih-Horng Shiao
(74) *Attorney, Agent, or Firm* — Ward and Smith, P.A.

(57) ABSTRACT

Methods and compounds for preventing or reducing the toxic side effects of cardiac glycosides by inhibiting the mitochondrial sodium-calcium exchanger (mNCE) are provided. Methods and compositions for preventing or reducing the occurrence of conditions associated with heart failure, including, but not limited to, sudden cardiac death and contractile decompensation, by inhibiting the mNCE also are provided.

18 Claims, 11 Drawing Sheets

Isoproterenol induced sudden death
(Acute SCD protocol)
(5 mg/kg iso was i.p. injected at 2 days after surgery)

|      | survivor | Sudden death |
|------|----------|--------------|
| -CGP | 3        | 10           |
| +CGP | 8        | 2            |

METHODS FOR TREATING HEART FAILURE BY INHIBITING THE MITOCHONDRIAL SODIUM-CALCIUM EXCHANGER (MNCE)

FEDERALLY SPONSORED RESEARCH OR DEVELOPMENT

This invention was made with United States Government support under P01 HL081427 awarded by the National Institutes of Health (NIH). The United States Government has certain rights in the invention.

CROSS-REFERENCE TO RELATED APPLICATIONS

This application is a 35 U.S.C. 371 U.S. national entry of International Application PCT/US2010/026890 having an international filing date of Mar. 11, 2010, which claims the benefit of U.S. Provisional Application Nos. 61/159,148, filed Mar. 11, 2009, and 61/250,729, filed Oct. 12, 2009, the content of each of the aforementioned applications is incorporated herein by reference in its entirety.

CROSS-REFERENCE TO RELATED APPLICATIONS

This application claims the benefit of U.S. Provisional Application Nos. 61/159,148, filed Mar. 11, 2009, and 61/250,729, filed Oct. 12, 2009, each of which is incorporated herein by reference in its entirety.

TECHNICAL FIELD

The presently disclosed subject matter relates to methods and compositions for treating heart failure by inhibiting the mitochondrial sodium-calcium exchanger (mNCE).

BACKGROUND

Chronic heart failure is one of the leading causes of morbidity and mortality in the United States. Although the mechanisms of heart failure (HF) have been studied extensively, mortality remains high and the aim of HF treatment in the clinic is focused on relieving symptoms, preventing hospitalization, and improving the quality of life of the patient. Four categories of drugs, including diuretics, inhibitors of renin-angiotensin-aldosterone system, beta-adrenergic receptor blockers, and cardiac glycosides, are currently recommended by The American College of Cardiology/American Heart Association Joint Guidelines for routine use to treat HF. Hunt, S. A., et al., *Circulation* 112(12):e154-235 (Sep. 20, 2005). Among these drugs, cardiac glycosides, including, but not limited to, digitoxin, digoxin, and ouabain, have been used for more than 200 years with multiple beneficial clinical effects. Treatment with digoxin can improve symptoms, increase cardiac output, enhance the quality of life, decrease cardiac decompensation, and decrease the need for and/or duration of hospitalization. The clinical use of digoxin has waned in recent years; however, due to its potentially toxic side effects and the finding that long term mortality is not significantly reduced.

SUMMARY

The presently disclosed subject matter provides methods and compounds for preventing or reducing toxic side effects of cardiac glycosides by inhibiting the mitochondrial sodium-calcium exchanger (mNCE). The mNCE is the main pathway in the heart mediating calcium efflux from the mitochondrial matrix. Inhibition of the mNCE ameliorates the negative effects of cardiac glycosides on cellular metabolism and redox status without diminishing the positive inotropic effects of the cardiac glycoside, thereby resulting in an improvement in function and preservation of cell viability without promoting potentially fatal arrhythmias. Thus, in some embodiments, the presently disclosed methods can improve the efficacy of cardiac glycosides as therapeutic agents in patients with chronic heart failure. In other embodiments, the presently disclosed subject matter provides methods and compositions for preventing or reducing the occurrence of conditions associated with heart failure, including, but not limited to, sudden cardiac death and contractile decompensation, by inhibiting the mNCE.

Accordingly, in one aspect, the presently disclosed subject matter provides a method for preventing, ameliorating, or reducing the severity of an adverse effect of a cardiac glycoside in a subject being treated with a cardiac glycoside for one or more conditions or symptoms associated with heart failure by administering to the subject a therapeutically effective amount of a mitochondrial sodium-calcium exchanger (mNCE) inhibitor of Formula I:

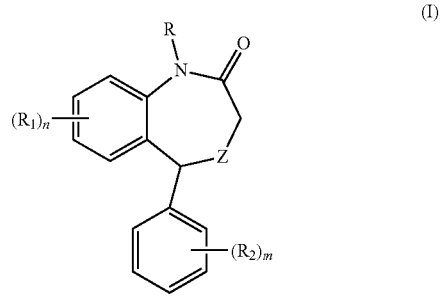

wherein:

m and n are the same or different and are integers independently selected from the group consisting of 0, 1, 2, 3, and 4;

Z is selected from the group consisting of O, S, and S(=O);

R is selected from the group consisting of H, alkyl, and substituted alkyl;

$R_1$ and $R_2$ are the same or different and at each occurrence are independently selected from the group consisting of halogen, alkyl, substituted alkyl, and nitro; and stereoisomers, prodrugs, or pharmaceutically acceptable salts thereof.

In certain aspects, the mNCE inhibitor is 7-chloro-5-(2-chlorophenyl)-1,5-dihydro-4,1-benzothiazepin-2(3H)-one (CGP-37157) and the cardiac glycoside with which the subject is being treated can include ouabain, digoxin, digitoxin, or oleandrin.

In a second aspect, the presently disclosed subject matter provides a method for treating heart failure by administering to a subject having, suspected of having, or at risk of having heart failure, a therapeutically effective amount of one or more cardiac glycosides and a therapeutically effective amount of a mitochondrial sodium-calcium exchanger (mNCE) inhibitor of Formula I.

In a third aspect, the presently disclosed subject matter provides a method for treating heart failure by administering to a subject having, suspected of having, or at risk of having heart failure a therapeutically effective amount of a mitochondrial sodium-calcium exchanger (mNCE) inhibitor of Formula I. In certain aspects, the method of treating includes preventing, ameliorating, or improving one or more conditions or symptoms associated with heart failure, including, but not limited to, sudden cardiac death, contractile decompensation, fractional shortening (FS), proarrhythmia, and arrhythmia.

In a fourth aspect, the presently disclosed subject matter provides a pharmaceutical composition comprising at least one cardiac glycoside and at least one mitochondrial sodium-calcium exchanger (mNCE) inhibitor of Formula I.

In a fifth aspect, the presently disclosed subject matter provides a kit comprising an amount of an mNCE inhibitor of Formula I in a first unit dosage form and an amount of a cardiac glycoside in a second unit dosage form.

In yet another aspect, the presently disclosed subject matter provides compounds and compositions for use as a medicament, preferably a human medicament. In other aspects, the presently disclosed subject matter provides for the use of the presently disclosed compounds and compositions in the manufacture or preparation of a medicament for treating heart failure by inhibiting the mNCE.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
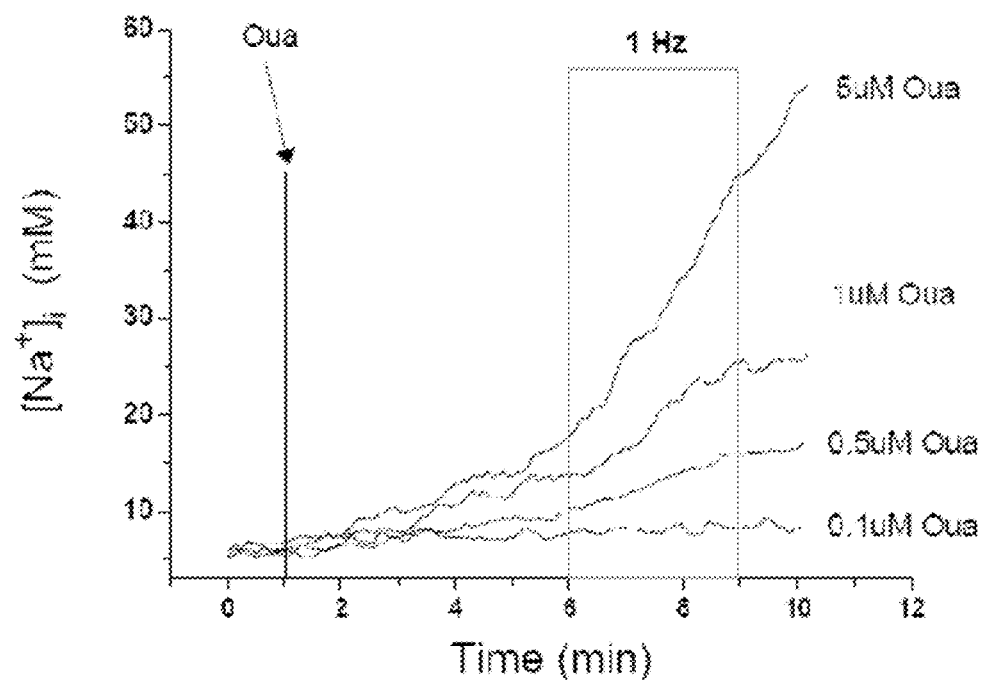
Figure 2:
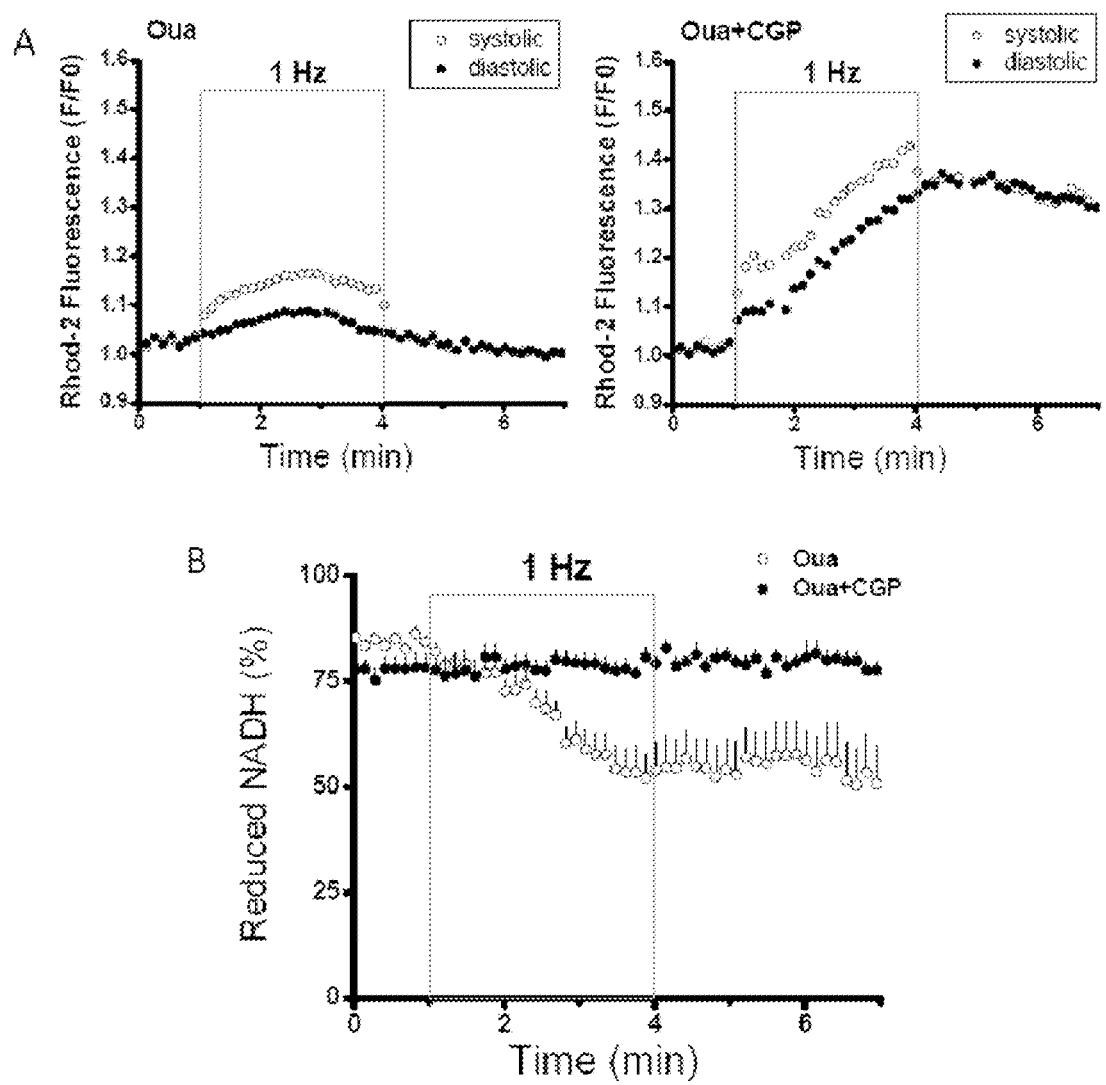
Figure 3:
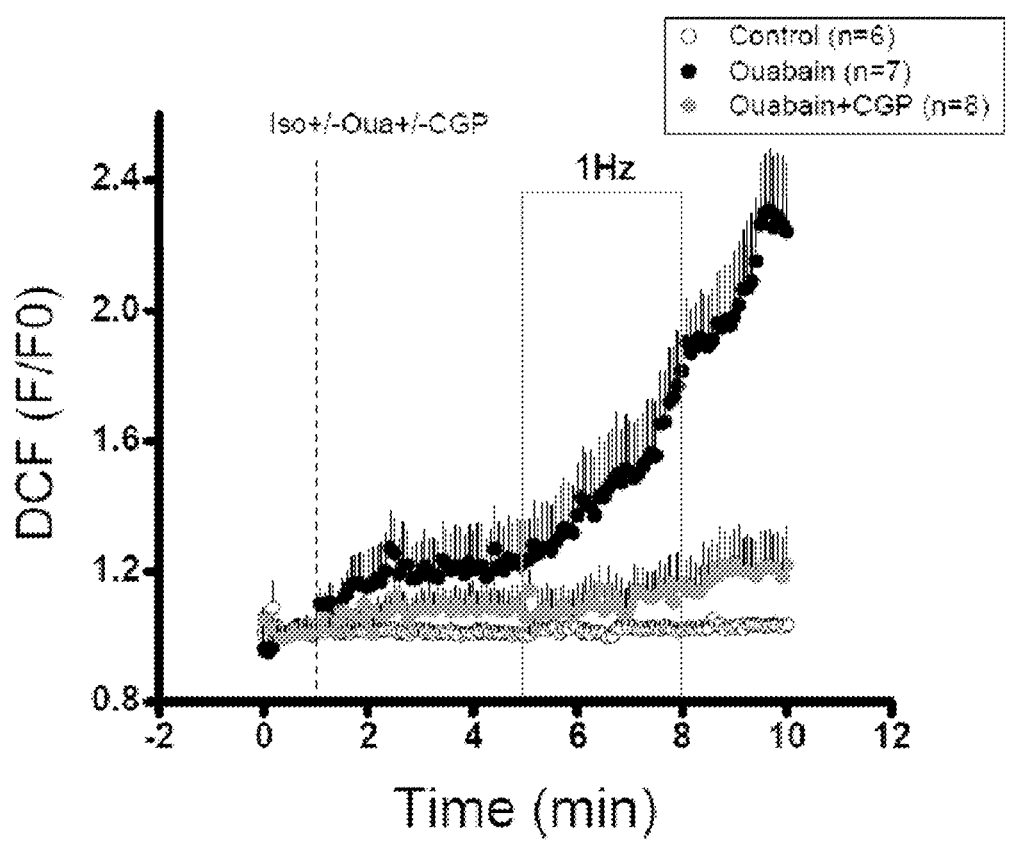
Figure 5:
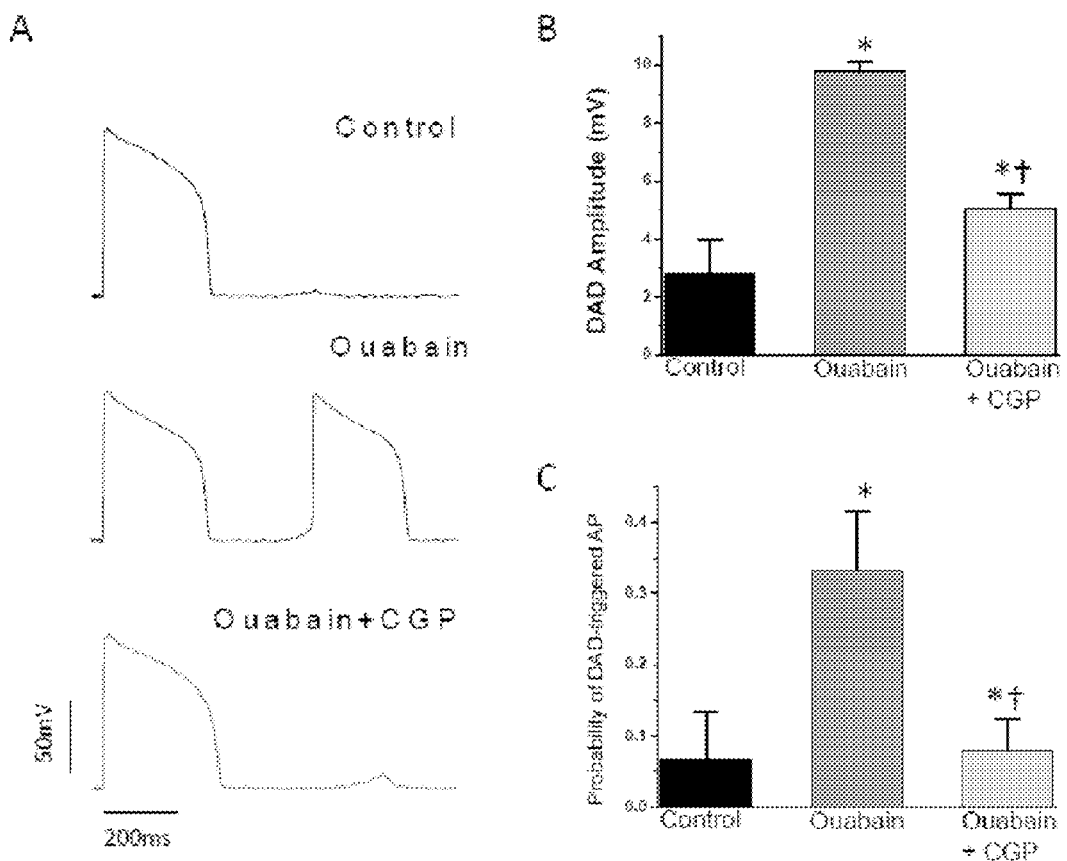
Figure 6:
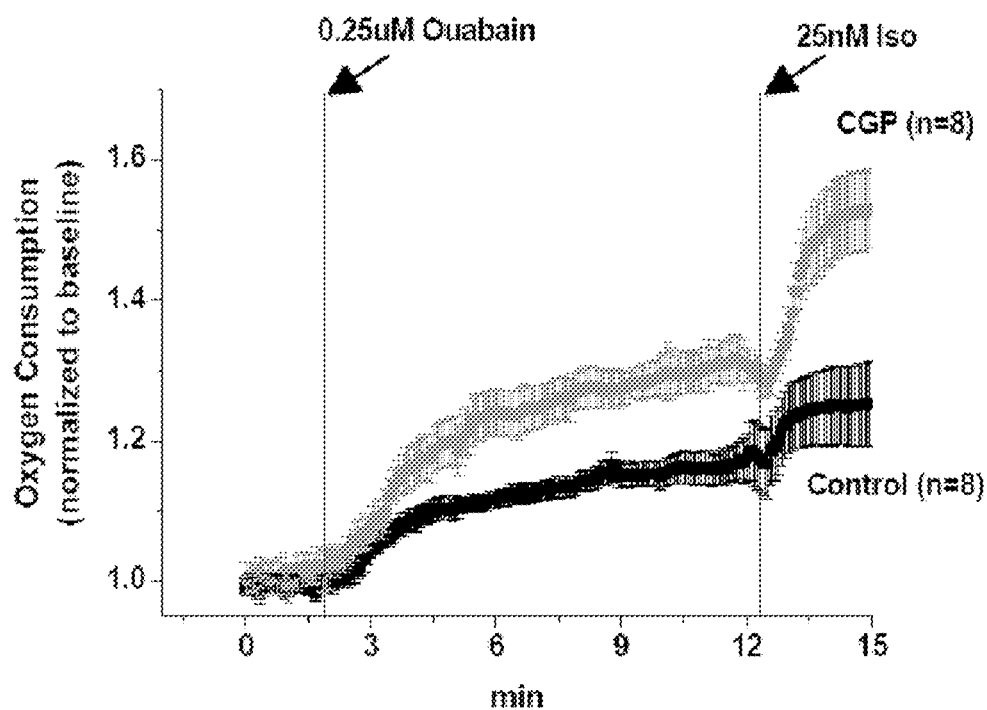
Figure 8:
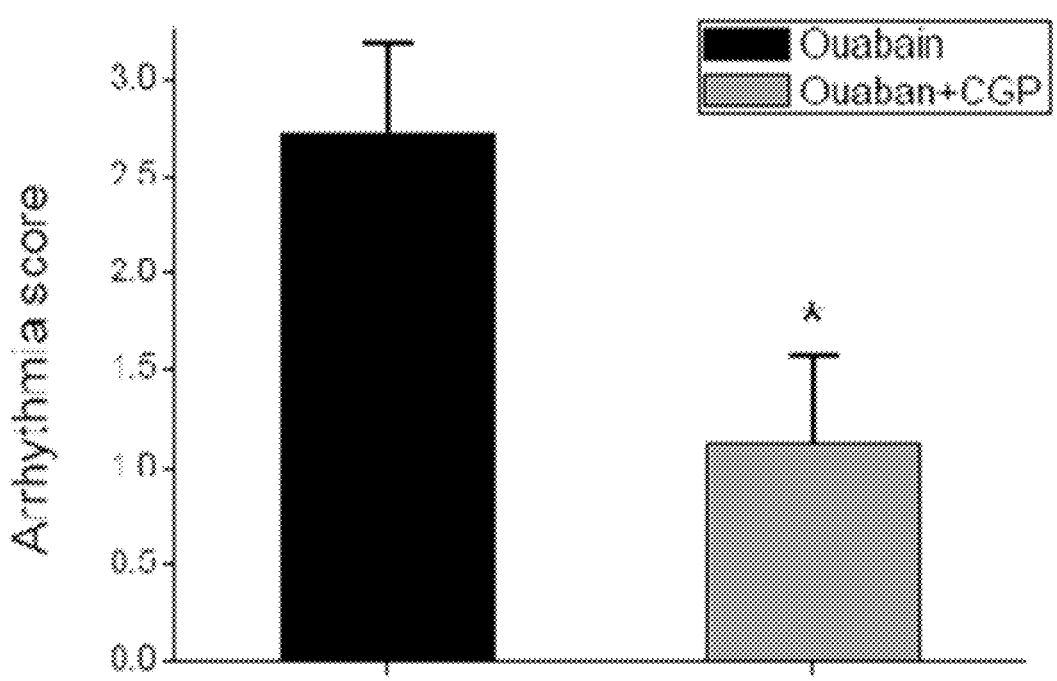
Figure 10:
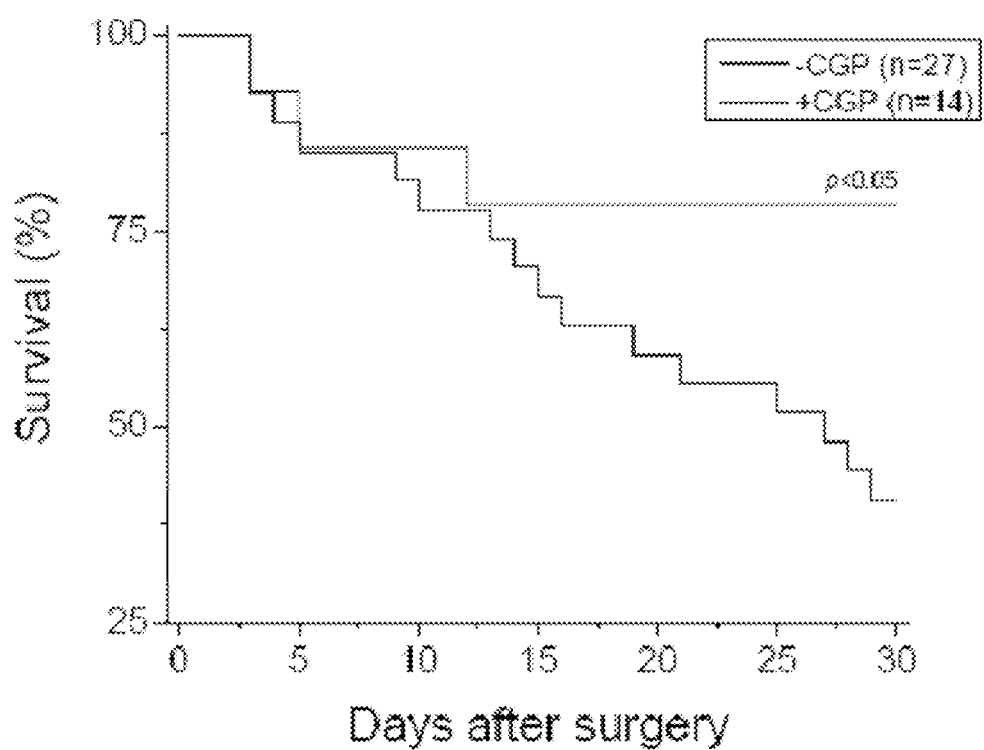
Figure 11:
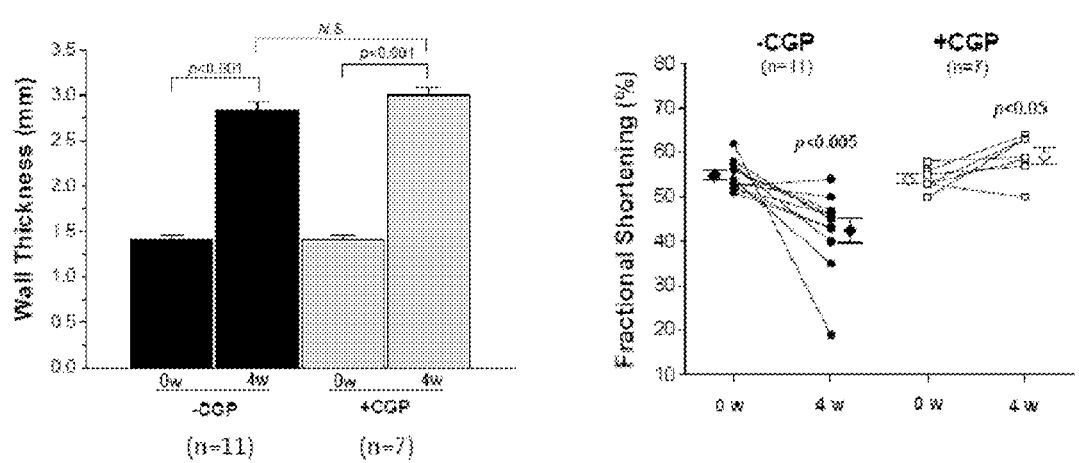

Having thus described the presently disclosed subject matter in general terms, reference will now be made to the accompanying Drawings, which are not necessarily drawn to scale, and wherein:

FIG. 1 shows representative recordings of $[Na^+]_i$. Isolated cardiac myocytes were loaded with sodium-binding benzofuran isophthalate (SBFI)-AM. After a one-minute recording, cells were treated with 100-nM isoproterenol and ouabain at different concentrations as indicated for five minutes, and then were field-stimulated at 1 Hz for three minutes (boxed area). After stimulation, cells were recorded at rest for one minute;

FIGS. 2A and 2B show the effect of ouabain and CGP-37157 on mitochondrial $Ca^{2+}$ accumulation and NADH production. After a four-minute treatment of 100-nM isoproterenol and 1-µM ouabain with (n=9) or without (n=11) CGP-37157, rhod-2 (A) and NADH (B) signals were recorded at resting state for one minute, followed by stimulation at 1 Hz for three minutes (boxed area), and then returned to resting state for another one minute recording;

FIG. 3 shows the effects of ouabain and CGP-37157 on reactive oxygen species (ROS) production. Dichlorofluorescein (DCF) fluorescence was recorded in three groups of cells. 100-nM isoproterenol with or without 1-µM ouabain and 1-µM CGP-37157 were added at the dashed line. Cells were field-stimulated at 1 Hz for three minutes during recording (boxed area). Control cells were only treated with 100-nM isoproterenol;

FIGS. 4A-4C show the effects of ouabain and CGP-37157 on $[Ca^{2+}]_c$ cycling. Isolated cardiac myocytes were loaded with indo-1 AM. After a five-minute treatment of 100-nM isoproterenol with or without ouabain and CGP-37157, cells were field stimulated for three minutes: (A) representative $[Ca^{2+}]_c$ traces at the beginning (left panels) and end of stimulation (right panels); (B) the average $\Delta[Ca^{2+}]_c$ recorded at the midpoint of stimulation is shown for control cells (n=3), ouabain treated cells (n=12), and ouabain plus CGP-37157 treated cells (n=12). *p<0.01 while compared to control; † p<0.05 while compared to ouabain treated group; and (C) the average of diastolic $[Ca^{2+}]_c$ recorded in control (isoproterenol only), ouabain-treated, and ouabain plus CGP-37157-treated cells;

FIGS. 5A-5C show the effects of ouabain and CGP-37157 on delayed afterdepolarizations (DADs). In the presence of 100-nM isoproterenol, current-clamped cells were treated with 1-µM ouabain with or without 1-µM CGP-37157 for five minutes, and action potentials (APs) were recorded at 1 Hz for three minutes: (A) representative AP traces; (B) amplitude of DADs; and (C) probability of DAD-triggered AP activation. *p<0.01 compared to control; † p<0.01 compared to ouabain-treated group;

FIG. 6 shows oxygen consumption in isolated perfused hearts. Measurements of oxygen consumption are displayed before and after application of ouabain and isoproterenol with (n=8) or without (n=8) CGP-37157, showing their effects on oxygen consumption;

FIGS. 7A-7F show representative tracings of LV pressure and ECG waveforms recorded at the end of baseline recording (A and B), at the end of ten-minute ouabain application (C and D), and at the time point of transition to VF after isoproterenol administration (E and F). A, C, and E were recorded in a heart without CGP-37157 treatment. B, D, and F were recorded in a CGP-37157 treated heart that underwent VF;

FIG. 8 shows a comparison of arrhythmia scores. Arrhythmia scores were tabulated for the ten-minute ouabain treatment period for hearts treated with (n=8) or without (n=8) CGP-37157 (*p<0.01);

FIG. 9 is a chart showing isoproterenol-induced sudden cardiac death using the presently disclosed acute sudden cardiac death protocol, wherein 5-mg/kg isoproterenol was injected intraperitoneally two days after ascending aortic banding. Legend: –CGP indicates the group of animals that did not receive CGP-37157 treatment and +CGP indicates the group of animals that received CGP-37157 treatment;

FIG. 10 is a graph showing the survival rate of aorta banding Guinea pig subjects using the presently disclosed delayed sudden cardiac death (SCD) protocol with and without CGP-37157 treatment, wherein isoproterenol was administered with an intraperitoneal injection of 1 mg/kg for the first week and 2 mg/kg for another four weeks; and FIG. 11 shows representative results from echocardiographic studies carried out before (0 w) and at four weeks (4 w) after aortic banding of Guinea pig subjects using the presently disclosed delayed SCD protocol measuring hypertrophic response and in vivo hemodynamics with and without CGP-37157 treatment, including measurements of left ventricular wall thickness (left panel) and Fractional Shortening (FS) (right panel). Legend: –CGP indicates the group of animals that did not receive CGP-37157 treatment and +CGP indicates the group of animals that received CGP-37157 treatment.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

I. Methods and Compositions for Preventing Digitalis Toxicity by Inhibiting
Mitochondrial Sodium-Calcium Exchange Treatment of heart failure with cardiac glycosides, for example, digitalis glycosides, can improve symptoms, increase cardiac output, enhance quality of life, and decrease clinical decompensation and hospitalization. See Rahimtoola, S. H., "Digitalis therapy for patients in clinical heart failure," *Circulation* 109(24):2942-2946 (Jun. 22, 2004). The primary action of cardiac glycosides is their ability to inhibit $Na^+/K^+$-ATPase (NKA), which elicits multiple effects on cardiac physiology and pathology. Gheorghiade, M., et al., "Digoxin in the management of cardiovascular disorders," *Circulation* 109(24):2959-2964 (Jun. 22, 2004). Inhibition of NKA on the sarcolemma of cardiac myocytes has a positive inotropic effect, mediated by an elevation of intracellular $Na^+$ ($[Na^+]_i$). Elevated $[Na^+]_i$ increases sarcoplasmic reticulum (SR) $Ca^{2+}$ load by affecting the activity of the sodium/calcium exchanger (NCX) on the sarcolemma, as a consequence of a reduction of the driving force for $Ca^{2+}$ extrusion and/or an increase in $Ca^{2+}$ influx via the NCX. The resulting increase of SR $Ca^{2+}$ load is responsible not only for the inotropic effect, but also is responsible for the arrhythmogenic effects of glycosides, which is the major adverse effect of digitalis drugs.

Besides its inotropic effect, clinical trials have shown that digitalis glycosides also could reduce plasma norepinephrine levels, see Ribner, H. S., et al., "Acute effects of digoxin on total systemic vascular resistance in congestive heart failure due to dilated cardiomyopathy: a hemodynamic-hormonal study," *Am. J. Cardiol.*, 56(13):896-904 (Nov. 15, 1985); van Veldhuisen, D. J., "Double-blind placebo-controlled study of ibopamine and digoxin in patients with mild to moderate heart failure: results of the Dutch Ibopamine Multicenter Trial (DIMT)," *JACC*, 22(6):1564-1573 (Nov. 15, 1993); and Alicandri C., et al., "Captopril versus digoxin in mild-moderate chronic heart failure: a crossover study," *J. Cardiovasc. Pharmacol.*, 9 Suppl 2:S61-67 (1987), serum aldosterone, Ribner et al., supra, Alicandri et al., supra, and Covit, A. B., et al., "Suppression of the renin-angiotensin system by intravenous digoxin in chronic congestive heart failure," *Am. J. Med.*, 75(3):445-447 (September 1983), and plasma renin activity, Ribner et al., supra and Covit et al., supra, in patients with HF. The beneficial effects of glycosides on HF are most likely attributable to both their inotropic and neurohormonal effects. The adverse effects of glycosides, which include cardiac arrhythmias, gastrointestinal symptoms, and central nervous system abnormalities, also have been well documented. Hunt et al., supra.

It is thought that glycosides might impair mitochondrial energetics in cardiac myocytes due to elevated $[Na^+]_i$. Maack C., et al., "Elevated cytosolic $Na^+$ decreases mitochondrial $Ca^{2+}$ uptake during excitation-contraction coupling and impairs energetic adaptation in cardiac myocytes," *Circ. Res.*, 99(2):172-182 (Jul. 21, 2006); Liu T. and O'Rourke B., "Enhancing mitochondrial $Ca^{2+}$ uptake in myocytes from failing hearts restores energy supply and demand matching," *Circ. Res.*, 103(3):279-288 (Aug. 1, 2008). Mitochondrial $Ca^{2+}$ ($[Ca^{2+}]_m$) homeostasis plays a central role in energy supply and demand matching. Increased cardiac work leads to an increase in $[Ca^{2+}]_m$ accumulation, Maack et al., supra, which is critical for maintaining $NAD^+/NADH$ redox potential, Maack et al., supra, Liu and O'Rourke, supra, by activating several enzymes in the tricarboxylic acid cycle. McCormack, J. G., et al., "Role of calcium ions in regulation of mammalian intramitochondrial metabolism," *Physiol. Rev.*, 70(2):391-425 (April 1990).

Mitochondria have several functions beyond ATP production, including acting as an intracellular $Ca^{2+}$ buffering system. Elevated $[Na^+]_i$ blunts $[Ca^{2+}]_m$ accumulation by activating the mitochondrial $Na^+/Ca^{2+}$ exchanger (mNCE), the major $[Ca^{2+}]_m$ efflux pathway, and therefore mediates net oxidation of NADH during increased work. Recent studies have demonstrated this adverse effect of elevated $[Na^+]_i$ on mitochondrial energetics in normal cardiac myocytes, with $[Na^+]_i$ elevated artificially using the patch clamp technique, and in myocytes isolated from failing hearts, with a chronic pathological elevation of $[Na^+]_i$. Maack et al., supra; Liu and O'Rourke, supra.

It has been shown that inhibition of $[Ca^{2+}]_m$ efflux by CGP-37157 increases mitochondrial $Ca^{2+}$ retention capacity and consequently decreases cytosolic $Ca^{2+}$ ($[Ca^{2+}]_c$) cycling. Maack et al., supra, and that CGP-37157 enhances $[Ca^{2+}]_m$ accumulation and restores mitochondrial NADH production in cells with elevated $[Na^+]_i$. Liu and O'Rourke, supra. It also has been shown that elevated $[Na^+]_i$ compromises mitochondrial energetics and redox balance by blunting mitochondrial $Ca^{2+}$ ($[Ca^{2+}]_m$) accumulation, and that inhibition of the mitochondrial $Na^+/Ca^{2+}$ exchanger (mNCE) reverses this impairment. Liu and O'Rourke, supra.

Accordingly, in some embodiments, the presently disclosed subject matter demonstrates that cardiac glycosides, including, but not limited to, ouabain, have an adverse effect on cardiac energetics due to elevated $[Na^+]_i$, and that the presently disclosed mNCE inhibitors, including, but not limited to, CGP-37157, can inhibit this effect to improve energy supply and demand imbalance. Moreover, the presently disclosed subject matter demonstrates the effects of mNCE inhibitors on glycoside-induced irregular $[Ca^{2+}]_c$ cycling in isolated myocytes and on glycoside-induced arrhythmias in isolated perfused hearts. In other embodiments, the presently disclosed subject matter demonstrates that the toxicity and arrhythmogenic effects of cardiac glycosides, through elevated $[Na^+]_i$, can be attributed to altered mitochondrial function and that these effects can be prevented by mNCE inhibitors.

Generally, the presently disclosed subject matter demonstrates that an mNCE inhibitor, including, but not limited to CGP-37157, can prevent the adverse effects of cardiac glycosides on mitochondrial energetics and oxidative stress. Further, the inotropic and respiratory responses to cardiac glycosides, e.g., ouabain, and $\beta_1$-adrenergic receptor agonists, e.g., isoproterenol (4-[1-hydroxy-2-(isopropylamino)ethyl] benzene-1,2-diol), can be enhanced by an mNCE inhibitor, e.g., CGP-37157.

The presently disclosed subject matter indicates that an improvement of mitochondrial $Ca^{2+}$ retention by mNCE inhibition can be beneficial for mitigating the toxic effects of cardiac glycosides, particularly with respect to the suppression of $Ca^{2+}$-triggered arrhythmias, while enhancing their positive inotropic action.

Accordingly, in some embodiments, the presently disclosed subject matter provides a method for preventing, ameliorating, or reducing the severity of an adverse effect of a cardiac glycoside in a subject being treated with a cardiac glycoside for one or more conditions or symptoms associated with heart failure, the method comprising administering to the subject a therapeutically effective amount of a mitochondrial sodium-calcium exchanger (mNCE) inhibitor, wherein the mNCE inhibitor comprises a compound of Formula I:

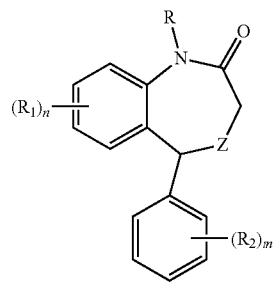

wherein:

m and n are the same or different and are integers independently selected from the group consisting of 0, 1, 2, 3, and 4;

Z is selected from the group consisting of O, S, and S(=O);

R is selected from the group consisting of H, alkyl, and substituted alkyl;

$R_1$ and $R_2$ are the same or different and at each occurrence are independently selected from the group consisting of halogen, alkyl, substituted alkyl, and nitro; and stereoisomers, prodrugs, or pharmaceutically acceptable salts thereof.

While the following terms in relation to compounds of Formula I are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

A named "R" or group will generally have the structure that is recognized in the art as corresponding to a group having that name, unless specified otherwise herein. For the purposes of illustration, certain representative "R" groups as set forth above are defined below.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

A structure represented generally by the formula:

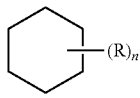

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

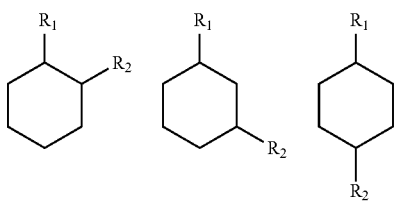

and the like.

The terms "halo", "halide", or "halogen" as used herein refer to fluoro, chloro, bromo, and iodo groups.

The term "nitro" refers to the —$NO_2$ group.

Throughout the specification and claims, a given chemical formula or name shall encompass all tautomers, congeners, and optical- and stereoisomers, as well as racemic mixtures where such isomers and mixtures exist.

More particularly, representative compounds of Formula I are disclosed in U.S. Patent Application Publication No. US2002/0082193 A1, to Anderson et al., published Jun. 27, 2002, which is incorporated herein by reference in its entirety.

In particular embodiments of compounds of Formula I, Z is sulfur, R is hydrogen, $R_1$ and $R_2$ are each chlorine, m and n are each one, and the compound of Formula I is CGP-37157 (7-chloro-5-(2-chlorophenyl)-1,5-dihydro-4,1-benzothiazepin-2(3H)-one), which has the following structure:

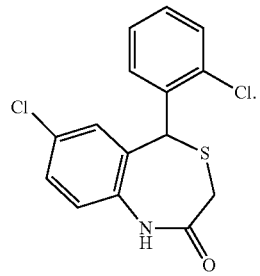 [SMILES: O=C1CSC(c2ccccc2Cl)c2cc(Cl)ccc2N1]

One of ordinary skill in the art upon review of the presently disclosed subject matter would recognize that derivatives, analogs, and congeners of CGP-37157, in addition to compounds disclosed in U.S. Patent Application Publication No. US2002/0082193 A1, also are suitable for use with the presently disclosed methods.

As used herein, an "analog" refers to a chemical compound in which one or more individual atoms or functional groups of a parent compound have been replaced, either with a different atom or with a different functional group. For example, thiophene is an analog of furan, in which the oxygen atom of the five-membered ring is replaced by a sulfur atom. As used herein, a "derivative" refers to a chemical compound which is derived from or obtained from a parent compound and contains essential elements of the parent compound but typically has one or more different functional groups. Such functional groups can be added to a parent compound, for example, to improve the molecule's solubility, absorption, biological half life, and the like, or to decrease the toxicity of the molecule, eliminate or attenuate any undesirable side effect of the molecule, and the like. An example of a derivative is an ester or amide of a parent compound having a carboxylic acid functional group. The term "congener" refers to one or more chemical compounds which differ only by the number and position(s) of particular a substituent group, e.g., a halogen group, on a ring. Commonly known congeners are, for example, polychlorinated biphenyls, which differ only by the number and position of chlorine atoms on a biphenyl ring structure.

The cardiac glycoside with which the subject is being treated can be any cardiac glycoside known in the art that is used or being contemplated for use in treating heart failure or a condition of symptom associated with heart failure. Representative cardiac glycosides include, but are not limited to, ouabain, digoxin, digitoxin, oleandrin, and combinations thereof. Accordingly, in some embodiments the cardiac glycoside includes one or more glycosides extracted from plants comprising the digitalis genus. Additional cardiac glycosides derived from various natural sources are disclosed in U.S. Patent Application Publication No. US2004/0082521 A1, to Singh, published Apr. 29, 2004, which is incorporated herein by reference in its entirety, and include, but are not limited to, neriifolin, odoroside A and H, cymarin, sarmentocymarin, periplocymarin, K-strophantin, thevetin A, cerberin, peruvoside, thevetosin, thevetin B, tanghinin, deacetyltanghinin, echujin, hongheloside G, honghelin, periplocin, strophantidol, nigrescin, uzarin, calotropin, cheiroside A, cheirotoxin, euonoside, euobioside, euomonoside, lancetoxin A and B, kalanchoside, bryotoxin A-C, bryophyllin B, cotiledoside, tyledoside A-D, F and G, orbicuside A-C, alloglaucotoxin, corotoxin, coroglaucin, glaucorin, scillarene A and B, scilliroside, scilliacinoside, scilliglaucoside, scilliglaucosidin, scillirosidin, scillirubrosidin, scillirubroside, proscillaridin A, rubelin, convalloside, convallatoxin, bovoside A, glucobovoside A, bovoruboside, antiarin A, helleborin, hellebrin, adonidin, adonin, adonitoxin, thesiuside, gitoxin, gitalin, F-gitonin, digitonin, lanatoside A-C, bufotalin, bufotalinin, bufotalidin, pseudobufotalin, acetyl-digitoxin, acetyl-oleandrin, beta-methyldigoxin and alpha-methyldigoxin.

In some embodiments, the cardiac glycoside is ouabain (g-strophanthin or 1β,3β,5β,11α,14,19-Hexahydroxycard-20(22)-enolide 3-(6-deoxy-α-L-mannopyranoside or 4-[(1R,3S,5S,8R,9S,10R,11R,13R,14S,17R)-1,5,11,14-tetrahydroxy-10-(hydroxymethyl)-13-methyl-3-((2R,3R,4R,5R,6S)-3,4,5-trihydroxy-6-methyltetrahydro-2H-pyran-2-yloxy)hexadecahydro-1H-cyclopenta[a]phenanthren-17-yl]furan-2(5H)-one)), which is represented by the following chemical structure:

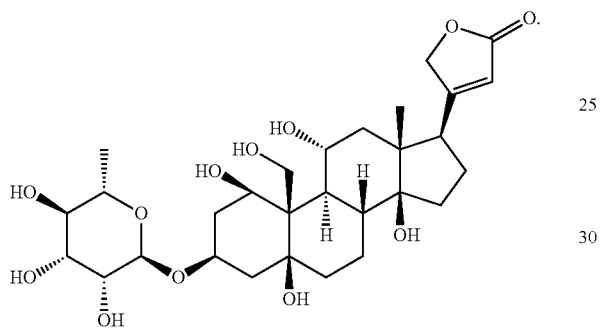

In other embodiments, the cardiac glycoside is digoxin (4-[(3S,5R,8R,9S,10S,12R,13S,14S)-3-[(2S,4S,5R,6R)-5-[(2S,4S,5R,6R)-5-[(2S,4S,5R,6R)-4,5-dihydroxy-6-methyl-oxan-2-yl]oxy-4-hydroxy-6-methyl-oxan-2-yl]oxy-4-hydroxy-6-methyl-oxan-2-yl]oxy-12,14-dihydroxy-10,13-dimethyl-1,2,3,4,5,6,7,8,9,11,12,15,16,17-tetradecahydrocyclopenta[a]phenanthren-17-yl]-5H-furan-2-one), which is represented by the following chemical structure:

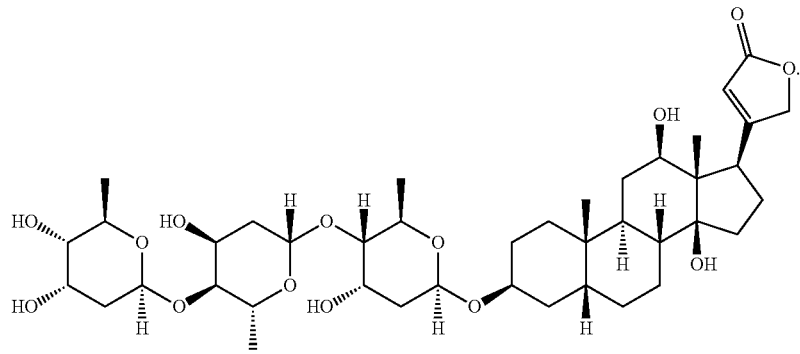

In yet other embodiments, the cardiac glycoside is digitoxin ((3β,5β)-3-[(O-2,6-dideoxy-β-D-ribo-hexapyranosyl-(1→4)-2,6-dideoxy-β-D-ribo-hexopyranosyl)oxy]-14-hydroxycard-20(22)-enolide), which is represented by the following chemical structure:

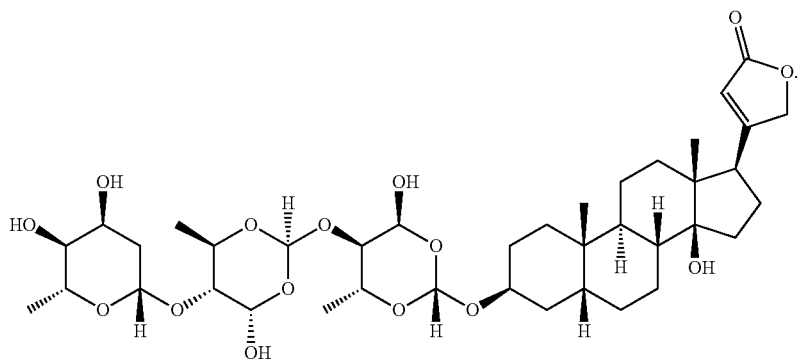

In some embodiments, the cardiac glycoside is oleandrin (acetic acid [(3S,5R,10S,13R,14S,16S,17'R)-14-hydroxy-3-[[(2R,4S,5S,6S)-5-hydroxy-4-methoxy-6-methyl-2-tetrahydropyranyl]oxy]-10,13-dimethyl-17-(5-oxo-2H-furan-3-yl)-1,2,3,4,5,6,7,8,9,11,12,15,16,17-tetradecahydrocyclopenta[a]phenanthren-16-yl]ester), which can be represented by the following chemical structure:

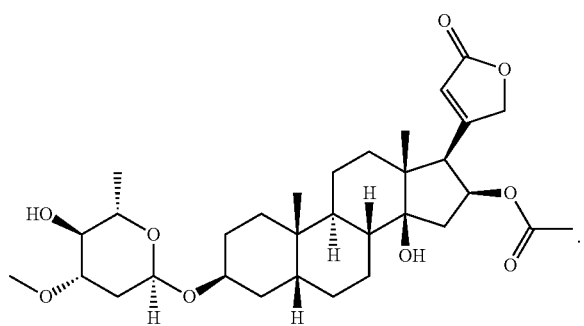

Extracts containing oleandrin have been put forward as tumor suppressors, antiviral agents or HF therapies; for example, as described in Mekhail T., et al., "Phase 1 trial of Anvirzel™ in patients with refractory solid tumors," *Invest. New Drugs* 24: 423-427 (2006), which is incorporated herein by reference in its entirety.

The use of cardiac glycosides in treating heart failure can result in several adverse effects, e.g., side effects, including, but not limited to, arrhythmia, proarrythmia, delayed afterdepolarizations (DADs), ventricular fibrillation, cardiac cell injury, and cardiac cell toxicity. Additional adverse effects of cardiac glycoside treatment include, but are not limited to: cardiovascular effects, such as conduction disturbances, atrioventricular block, atrial tachycardia, junctional tachycardia and ventricular arrhythmias, such as ventricular premature contractions and ventricular tachycardia; gastrointestinal side effects, such as nausea, vomiting, diarrhea or anorexia; and central nervous system effects, such as blurred vision, headaches, weakness, apathy and psychosis. Such side effects of cardiac glycosides can be mitigated by the presently disclosed methods, e.g., treatment with CGP-37157.

In addition to the side effects of cardiac glycosides on a subject, e.g., a patient being treated for heart failure, cardiac glycosides can cause detrimental changes in one or more physiological characteristics of a cardiomyocyte, i.e., a heart muscle cell, of the subject. As discussed in more detail hereinabove, such detrimental changes include elevating $[Na^+]_i$; suppressing $[Ca^{2+}]_m$ accumulation; decreasing NADH/NAD$^+$ redox potential; and increasing reactive oxygen species (ROS) levels.

The presently disclosed methods and compositions also include enhancing a positive inotropic effect of the cardiac glycoside by the addition of a compound of Formula I. In general, an inotrope is an agent that alters the force or energy of muscular contractions. More particularly, an inotropic agent alters the force or strength of the heart's muscular contractions, i.e., heartbeats. Two types of inotropic agents exist: negative and positive. Negative inotropic agents made the heart beat less strongly, whereas positive inotropic drugs make the heart beat more strongly. In general, calcium levels are increased by positive inotropic drugs and decreased by negative inotropic drugs.

In yet further embodiments, the presently disclosed subject matter further comprises improving or increasing cardiac oxygen consumption (VO$_2$) and/or one or more hemodynamic parameters of the subject being treated with a cardiac glycoside. Such hemodynamic parameters include, but are not limited to, an increase in left ventricular diastolic pressure (LVDP); an increase in contractility; an increase in the rate of contraction (+dP/dt); an increase in the rate of relaxation (-dP/dt); and combinations thereof.

The presently disclosed methods also include embodiments wherein the mNCE inhibitor increases or enhances one or more physiological conditions of a cardiomyocyte of the subject, including, but not limited to, enhancing mitochondrial $[Ca^{2+}]_m$ accumulation, increasing or restoring mitochondrial NADH production, increasing mitochondrial $[Ca^{2+}]_m$ retention capacity, and preventing cellular oxidative stress.

The presently disclosed methods also include embodiments wherein the mNCE inhibitor inhibits, decreases or attenuates one or more physiological conditions of a cardiomyocyte of the subject including, but not limited to, inhibiting $[Ca^{2+}]_m$ efflux, decreasing cytosolic $[Ca^{2+}]_c$ cycling, reducing accumulation of diastolic $[Ca^{2+}]_c$, reducing the incidence of discordant contractions, and Ca$^{2+}$ release.

In other embodiments, the presently disclosed subject matter includes a method for treating heart failure, the method comprising administering to a subject having, suspected of having, or at risk of having heart failure, a therapeutically effective amount of one or more cardiac glycosides and a therapeutically effective amount of a mitochondrial sodium-calcium exchanger (mNCE) inhibitor, wherein the mNCE inhibitor comprises a compound of Formula I:

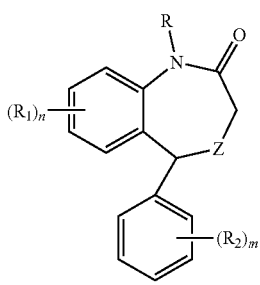

wherein:

m and n are the same or different and are integers independently selected from the group consisting of 0, 1, 2, 3, and 4;

Z is selected from the group consisting of O, S, and S(=O);

R is selected from the group consisting of H, alkyl, and substituted alkyl;

$R_1$ and $R_2$ are the same or different and at each occurrence are independently selected from the group consisting of halogen, alkyl, substituted alkyl, and nitro; and stereoisomers, prodrugs, or pharmaceutically acceptable salts thereof.

Representative compounds of Formula I are disclosed in U.S. Patent Application Publication No. US2002/0082193 A1, to Anderson et al., published Jun. 27, 2002, which is incorporated herein by reference in its entirety.

In particular embodiments of compounds of Formula I, Z is sulfur, R is hydrogen, $R_1$ and $R_2$ are each chlorine, m and n are each one, and the compound of Formula I is CGP-37157 (7-chloro-5-(2-chlorophenyl)-1,5-dihydro-4,1-benzothiazepin-2(3H)-one), which has the following structure:

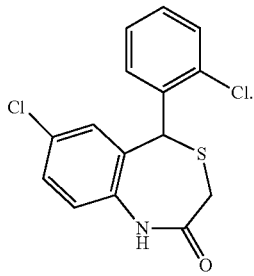 [SMILES: O=C1CSC(c2ccccc2Cl)c2cc(Cl)ccc2N1]

In some embodiments, the cardiac glycoside is selected from the group consisting of ouabain, digoxin, digitoxin, oleandrin, neriifolin, odoroside A and H, cymarin, sarmentocymarin, periplocymarin, K-strophantin, thevetin A, cerberin, peruvoside, thevetosin, thevetin B, tanghinin, deacetyl-tanghinin, echujin, hongheloside G, honghelin, periplocin, strophantidol, nigrescin, uzarin, calotropin, cheiroside A, cheirotoxin, euonoside, euobioside, euomonoside, lancetoxin A and B, kalanchoside, bryotoxin A-C, bryophyllin B, cotiledoside, tyledoside A-D, F and G, orbicuside A-C, alloglaucotoxin, corotoxin, coroglaucin, glaucorin, scillarene A and B, scilliroside, scilliacinoside, scilliglaucoside, scilliglaucosidin, scillirosidin, scillirubrosidin, scillirubroside, proscillaridin A, rubelin, convalloside, convallatoxin, bovoside A, glucobovoside A, bovoruboside, antiarin A, helleborin, hellebrin, adonidin, adonin, adonitoxin, thesiuside, gitoxin, gitalin, F-gitonin, digitonin, lanatoside A-C, bufotalin, bufotalinin, bufotalidin, pseudobufotalin, acetyl-digitoxin, acetyl-oleandrin, beta-methyldigoxin and alpha-methyldigoxin, and combinations thereof.

In the combination therapy disclosed immediately hereinabove, i.e., the combination of an mNCE inhibitor and a cardiac glycoside for treating heart failure, in some embodiments, the mNCE inhibitor has an additive effect in enhancing the positive inotropic effects of the cardiac glycoside. Thus, in some embodiments, the additive effect of the mNCE inhibitor can be realized in an increase in left ventricular diastolic pressure (LVDP); an increase in contractility; an increase in the rate of contraction (+dP/dt); an increase in the rate of relaxation (-dP/dt). This additive effect also can result in an increase in the maximal $VO_2$ response.

II. Prevention of Sudden Cardiac Death and Contractile Decompensation in Heart Failure by Inhibition of the Mitochondrial Sodium-Calcium Exchanger (mNCE)

Elevated cytosolic $Na^+$ associated with chronic heart failure or cardiac glycoside treatment impairs cardiac mitochondrial function and increases oxidative stress during times of increased workload. These changes correlate with the induction of triggered and reentrant arrhythmias and contractile dysfunction (pump failure) in isolated perfused hearts or intact animals. The detrimental effects on cellular and whole organ function can be prevented by partial inhibition of the mitochondrial $Na^+/Ca^{2+}$ exchanger (mNCE), through the enhancement of mitochondrial $Ca^{2+}$ accumulation and maintenance of the NAD(P)H redox state, thereby abrogating the increase in oxidative stress, as well as cytoplasmic $Ca^{2+}$ overload.

In some embodiments, as provided in Example 2 herein below, the presently disclosed subject matter demonstrates that inhibition of mNCE protects against sudden cardiac death and contractile decompensation associated with heart failure. Accordingly, the presently disclosed subject matter provides methods and pharmaceutical compositions for preventing cardiac glycoside toxicity and sudden cardiac death and contractile decompensation in heart failure by inhibiting the mitochondrial sodium-calcium exchanger (mNCE).

In some embodiments, the presently disclosed subject matter provides a method for treating heart failure, the method comprising administering to a subject having, suspected of having, or at risk of having heart failure, a therapeutically effective amount of a mitochondrial sodium-calcium exchanger (mNCE) inhibitor, wherein the mNCE inhibitor comprises a compound of Formula I:

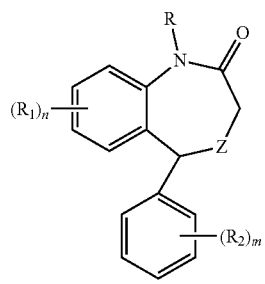

wherein:

m and n are the same or different and are integers independently selected from the group consisting of 0, 1, 2, 3, and 4;

Z is selected from the group consisting of O, S, and S(=O);

R is selected from the group consisting of H, alkyl, and substituted alkyl;

$R_1$ and $R_2$ are the same or different and at each occurrence are independently selected from the group consisting of halogen, alkyl, substituted alkyl, and nitro; and stereoisomers, prodrugs, or pharmaceutically acceptable salts thereof.

Representative compounds of Formula I are disclosed in U.S. Patent Application Publication No. US2002/0082193 A1, to Anderson et al., published Jun. 27, 2002, which is incorporated herein by reference in its entirety.

In particular embodiments of compounds of Formula I, Z is sulfur, R is hydrogen, $R_1$ and $R_2$ are each chlorine, m and n are each one, and the compound of Formula I is CGP-37157 (7-chloro-5-(2-chlorophenyl)-1,5-dihydro-4,1-benzothiazepin-2(3H)-one), which has the following structure:

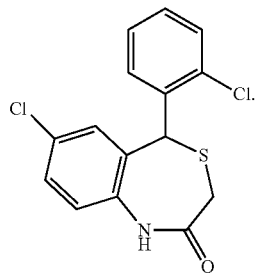 [SMILES: O=C1CSC(c2ccccc2Cl)c2cc(Cl)ccc2N1]

The presently disclosed methods can be used to treat a subject suffering from (i.e., having), suspected of having, or at risk of having or developing heart failure. The presently disclosed methods and compositions can be used to treat a subject in various stages of heart failure, including chronic heart failure, hypertrophic heart failure, and congestive heart failure. The term "heart failure" generally refers to one or more conditions in which the heart is no longer able to pump an adequate supply of blood in relation to the venous return and in relation to the metabolic needs of the tissues of the body at that particular moment. "Congestive heart failure" refers to that state in which abnormal fluid accumulation occurs in different parts of the body (e.g. swelling in limbs, pulmonary edema, pleural effusion) as the result of heart failure including, but not limited to, circulatory failure due to mechanical abnormalities, myocardial (muscular) failure, peripheral circulatory failure and cardiac, and non-cardiac circulatory overload.

Heart failure may ensue during the progression of ischemic heart disease, post myocardial infarction, hypertension, valvular heart disease or cardiomyopathy. The term heart failure can include different presentations of the disease, including, but not limited to, systolic heart failure (inability to develop enough force during systole); diastolic heart failure (inability to fully relax between beats); right-sided heart failure (failure of the right ventricle); left-sided heart failure (failure of the left ventricle); forward heart failure (inability to pump enough blood to meet the tissue demand during exercise or rest); backward heart failure (failure of the heart to supply enough blood to meet tissue demand when ventricular filling pressures are high); and high-output heart failure (although cardiac output may be normal, it is insufficient to meet an excessively high tissue demand).

Further, the presently disclosed methods and compositions can prevent, ameliorate, and/or improve one or more conditions or symptoms associated with heart failure. Such conditions or symptoms associated with heart failure include, but are not limited to, sudden cardiac death, contractile decompensation, fractional shortening (FS), proarrhythmia, arrhythmia, and combinations thereof. The presently disclosed methods and compositions also can prevent, ameliorate, and/or improve ancillary symptoms of heart failure occurring as a consequence of insufficient cardiac output, including dyspnea, persistent coughing or wheezing, tissue edema, fatigue, lack of appetite, nausea, confusion, and impaired thinking.

The term "sudden death" or "sudden cardiac death (SCD)" refers to a death, generally an unexpected death, due to cardiac causes that occurs in a short period of time (typically within one hour or less of the symptom onset) in a subject with known or previously undiagnosed cardiac disease. In many cases, sudden cardiac death is related to cardiac arrhythmias, including, but not limited to, tachyarrhythmias, such as ventricular fibrillation or ventricular tachycardia, and bradyarrhythmias.

Hypertrophic decompensation refers to the progression of cardiac hypertrophy, i.e., an increase in myocardial mass or an enlarging of the heart, from exhibiting normal function (i.e., hypertrophic compensation) to exhibiting a depressed function over time and ultimately clinically presenting symptoms of heart failure. At the cellular level, cardiac hypertrophy is manifested as an increase in cardiac myocyte size. Myocytes from decompensated hypertrophic hearts display impaired contractions, smaller and more prolonged $Ca^{2+}$ transients, and altered action potentials.

The term "fractional shortening" as used herein refers to a measure of left ventricular function and is determined by measuring the change in the diameter of the left ventricle between the contracted and relaxed states. More particularly, the percent fractional shortening is calculated as the difference between the left ventricle end-diastolic diameter (LVd) and the left ventricle end-systolic diameter (LVs) divided by the left ventricle end-diastolic diameter (LVd):

$$\frac{(LVd - LVs)}{LVd} * 100.$$

The term "proarrhythmia" refers to a new or more frequent occurrence of a pre-existing arrhythmia and is precipitated by anti-arrhythmic therapy. That is, it can be a side effect of anti-arrhythmic therapy with, for example, a cardiac glycoside. The term "arrhythmia" as used herein generally refers to a condition in which there is abnormal electrical activity in the heart causing the heart to beat too fast or too slowly, in which the heartbeat may be regular or irregular. Some arrhythmias are life-threatening and can result in cardiac arrest and sudden death, whereas other arrhythmias are minor and can be regarded as normal variants. Arrhythmia can be classified by rate, e.g., normal, tachycardia (greater than 100 beats/minute), and bradycardia (less than 60 beats/minute), or mechanism, e.g., automaticity, reentry, and fibrillation. The term "arrhythmogenesis" refers to the development of an arrhythmia.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The terms "treat" or "treating," and grammatical derivatives thereof, as used herein refer to any type of treatment that imparts a benefit to a subject afflicted with a disease or illness, including improvement in the condition of the subject (e.g., in one or more symptoms), delay in the progression of the condition, prevention or delay of the onset of the disease or illness, e.g., prophylactic treatment, enhancement of normal physiological functionality, and the like.

A "therapeutically effective amount" as provided herein refers to an amount of the presently disclosed compounds and/or compositions necessary to provide the desired therapeutic effect, e.g., an amount that is effective to prevent, alleviate, or ameliorate symptoms of disease or prolong the survival of the subject being treated. As would be appreciated by one of ordinary skill in the art upon review of the present disclosure, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The presently disclosed compound(s) can be administered therapeutically to achieve a therapeutic benefit or prophylactically to achieve a prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from a condition provides therapeutic benefit not only when the underlying condition is eradicated or ameliorated, but also when the patient reports a decrease in the severity or duration of the symptoms associated with the condition. Therapeutic benefit also includes halting or slowing the progression of the disease, regardless of whether improvement is realized by the patient.

For prophylactic administration, the presently disclosed compound(s) and compositions can be administered to a subject at risk of developing a particular condition, e.g., heart failure, or at risk to the toxic side effects of cardiac glycosides. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in an in vitro assay known in the art. Calculating dosages to achieve such circulating blood or serum concentrations taking into account the bioavailability of the particular compound is well within the capabilities of skilled artisans. For guidance, see Fingl & Woodbury, "General Principles," In: Goodman and Gilman's The Pharmaceutical Basis of Therapeutics, Chapter 1, pp. 1-46, latest edition, Pagamonon Press, and the references cited therein.

Initial dosages also can be estimated from in vivo data, such as animal models. Animal models useful for testing the efficacy of compounds to treat or prevent the various diseases described above are well-known in the art. Dosage amounts will depend on, among other factors, the activity of the compound, its bioavailability, the mode of administration and various factors discussed above. Dosage amount and interval can be adjusted individually to provide levels of the compound(s) sufficient to maintain a therapeutic or prophylactic effect. Skilled artisans will be able to optimize effective local dosages without undue experimentation.

The presently disclosed compound(s) and compositions can be administered once per day, a few or several times per day, or even multiple times per day, depending upon, among other things, the indication being treated and the judgment of the prescribing physician.

Preferably, the presently disclosed compound(s) and compositions will provide therapeutic or prophylactic benefit without causing substantial toxicity. Toxicity of the compound(s) and compositions can be determined using standard pharmaceutical procedures. The dose ratio between toxic and therapeutic (or prophylactic) effect is the therapeutic index. Compounds(s) and compositions that exhibit high therapeutic indices are preferred.

III. Pharmaceutical Compositions

In some embodiments, the presently disclosed subject matter provides a pharmaceutical composition comprising a therapeutically effective amount of at least one cardiac glycoside and a therapeutically effective amount of at least one mitochondrial sodium-calcium exchanger (mNCE) inhibitor, wherein the mNCE inhibitor comprises a compound of Formula I:

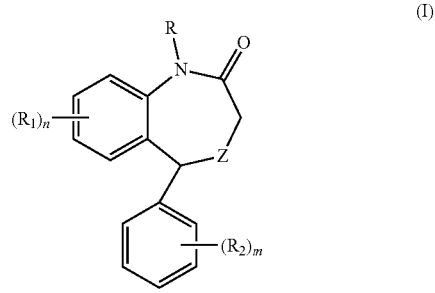

wherein:

m and n are the same or different and are integers independently selected from the group consisting of 0, 1, 2, 3, and 4;

Z is selected from the group consisting of O, S, and S(=O);

R is selected from the group consisting of H, alkyl, and substituted alkyl;

$R_1$ and $R_2$ are the same or different and at each occurrence are independently selected from the group consisting of halogen, alkyl, substituted alkyl, and nitro; and stereoisomers, prodrugs, or pharmaceutically acceptable salts thereof.

Representative compounds of Formula I are disclosed in U.S. Patent Application Publication No. US2002/0082193 A1, to Anderson et al., published Jun. 27, 2002, which is incorporated herein by reference in its entirety.

In particular embodiments of compounds of Formula I, Z is sulfur, R is hydrogen, $R_1$ and $R_2$ are each chlorine, m and n are each one, and the compound of Formula I is CGP-37157 (7-chloro-5-(2-chlorophenyl)-1,5-dihydro-4,1-benzothiazepin-2(3H)-one), which has the following structure:

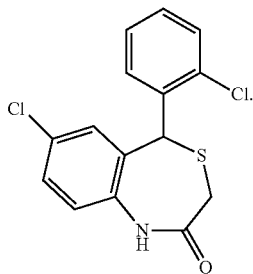 [SMILES: O=C1CSC(c2ccccc2Cl)c2cc(Cl)ccc2N1]

In some embodiments, the cardiac glycoside is selected from the group consisting of ouabain, digoxin, digitoxin, oleandrin, neriifolin, odoroside A and H, cymarin, sarmentocymarin, periplocymarin, K-strophantin, thevetin A, cerberin, peruvoside, thevetosin, thevetin B, tanghinin, deacetyl-tanghinin, echujin, hongheloside G, honghelin, periplocin, strophantidol, nigrescin, uzarin, calotropin, cheiroside A, cheirotoxin, euonoside, euobioside, euomonoside, lancetoxin A and B, kalanchoside, bryotoxin A-C, bryophyllin B, cotiledoside, tyledoside A-D, F and G, orbicuside A-C, alloglaucotoxin, corotoxin, coroglaucin, glaucorin, scillarene A and B, scilliroside, scilliacinoside, scilliglaucoside, scilliglaucosidin, scillirosidin, scillirubrosidin, scillirubroside, proscillaridin A, rubelin, convalloside, convallatoxin, bovoside A, glucobovoside A, bovoruboside, antiarin A, helleborin, hellebrin, adonidin, adonin, adonitoxin, thesiuside, gitoxin, gitalin, F-gitonin, digitonin, lanatoside A-C, bufotalin, bufotalinin, bufotalidin, pseudobufotalin, acetyl-digitoxin, acetyl-oleandrin, beta-methyldigoxin and alpha-methyldigoxin, and combinations thereof.

The compounds of Formula I, prodrugs, and the pharmaceutically acceptable salts thereof, as well as the presently disclosed cardiac glycosides, are referred to herein as "active compounds." Pharmaceutical compositions comprising the aforementioned active compounds also are provided herein. These pharmaceutical compositions comprise the presently disclosed active compounds in a pharmaceutically acceptable carrier. The term "pharmaceutically acceptable" with respect to a component, such as a salt, carrier, excipient or diluent of a composition according to the presently disclosed subject matter refers to a component that is compatible with the other ingredients of the composition in that it can be combined with the presently disclosed compounds without eliminating the therapeutic efficacy of the compounds and is suitable for use with subjects as provided herein without undue adverse side effects (including, but not limited to, toxicity, irritation, and allergic response) to the subject to which the particular compound is administered. Examples of pharmaceutically acceptable components include, without limitation, any of the standard pharmaceutical carriers, such as phosphate buffered saline solutions, water, emulsions such as oil/water emulsion, microemulsions, and various types of wetting agents.

Pharmaceutical formulations can be prepared for oral, intravenous, or aerosol administration as discussed in greater detail herein below. Also, the presently disclosed subject matter provides such active compounds that have been lyophilized and that can be reconstituted to form pharmaceutically acceptable formulations for administration, as by intravenous or intramuscular injection.

When used to treat or prevent conditions and diseases as described herein, the presently disclosed active compounds can be administered singly, as mixtures of one or more active compounds or in mixture or combination with other agents useful for treating such diseases and/or the symptoms associated with such diseases.

Further, in representative embodiments, certain compounds disclosed herein are prodrugs. The term "prodrug" refers to a therapeutic agent that has been chemically derivatized such that, upon administration to a subject, the derivative is metabolized to yield the biologically-active therapeutic agent. Accordingly, upon administration to a recipient, a prodrug is capable of providing (directly or indirectly) a compound of the presently disclosed subject matter or an inhibitorily active metabolite or residue thereof. Prodrugs can increase the bioavailability of the presently disclosed compounds when such compounds are administered to a subject (e.g., by allowing an orally administered compound to be more readily absorbed into the blood) or can enhance delivery of the parent compound to a biological compartment (e.g., the brain or lymphatic system) relative to a metabolite species.

The presently disclosed active compounds or prodrugs thereof can be formulated in the pharmaceutical compositions per se, or in the form of a hydrate, solvate, N-oxide or pharmaceutically acceptable salt, as is known in the art. Typically, such salts are more soluble in aqueous solutions than the corresponding free acids and bases, but salts having lower solubility than the corresponding free acids and bases also can be formed.

Such pharmaceutically acceptable salts include, but are not limited to, the gluconate, lactate, acetate, tartarate, citrate, phosphate, borate, nitrate, sulfate, and hydrochloride salts. Accordingly, pharmaceutically acceptable salts include acid addition salts, such as salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid, as well as other acid addition salts known in the art. The salts of the compounds described herein can be prepared by methods known in the art. For example, one or more equivalents of the base compound can be reacted with the desired acid in solution. After the reaction is complete, the salts can be crystallized from solution by the addition of an appropriate amount of solvent in which the salt is insoluble.

Pharmaceutical compositions comprising the presently disclosed active compounds (or prodrugs thereof) can be manufactured by means of conventional mixing, dissolving, granulating, dragee-making levigating, emulsifying, encapsulating, entrapping and/or lyophilization processes. The presently disclosed pharmaceutical compositions can be formulated in conventional manner using one or more physiologically acceptable carriers, diluents, excipients or auxiliaries that facilitate processing of the active compounds into preparations that can be used pharmaceutically.

Pharmaceutical compositions of the presently disclosed subject matter can take a form suitable for virtually any mode of administration, including, for example, topical, ocular, oral, baccal, systemic, nasal, pulmonary, transdermal, transmucosal, rectal, vaginal, injection, and the like, or a form suitable for administration by inhalation or insufflation. Pharmaceutical compositions designed for administration by injection, include, but are not limited to, subcutaneous, intravenous, intramuscular, intrathecal or intraperitoneal injection.

Useful injectable compositions include sterile suspensions, solutions or emulsions of the active compound(s) in aqueous or oily vehicles. The compositions also can contain formulating agents, such as suspending, stabilizing and/or dispersing agent. The compositions suitable for injection can be presented in unit dosage form, e.g., in ampules or in multidose containers, and can contain added preservatives. Alternatively, an injectable composition can be provided in powder form for reconstitution with a suitable vehicle, including, but not limited to, sterile water, buffer, dextrose solution, and the like, before use. To this end, the active compound(s) can be dried by any art-known technique, such as lyophilization, and reconstituted prior to use.

For oral administration, the pharmaceutical compositions can take the form of, for example, lozenges, tablets or capsules prepared by conventional means with pharmaceutically acceptable excipients, such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate. Preparations for oral administration can be suitably formulated to give controlled release of the active compound or prodrug, as is well known.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s) and compositions. Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475, each of which is incorporated herein by reference in its entirety.

In addition to compounds of Formula I or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain anti-microbial preservatives. Useful anti-microbial preservatives include methylparaben, propylparaben, and benzyl alcohol. The anti-microbial preservative is typically employed when the formulation is placed in a vial designed for multi-dose use.

The pharmaceutical formulations described herein can be lyophilized using techniques well known in the art. In such embodiments, the compound or salt is provided in the form of a lyophilizate, which is capable of being reconstituted with a suitable pharmaceutically acceptable carrier to form a liquid formulation suitable for injection thereof into a subject.

IV. Kits

In yet another aspect of the subject matter described herein, there is provided a stable, sterile formulation comprising a compound of Formula I, or a prodrug or a pharmaceutically acceptable salt thereof, in a unit dosage form in a sealed container. More particularly, the presently disclosed subject matter can include (a) an amount of an mNCE inhibitor, wherein the mNCE inhibitor is a compound of Formula I or a prodrug or a pharmaceutically acceptable salt thereof in a first unit dosage form; and (b) an amount of a cardiac glycoside in a second unit dosage form. The cardiac glycoside included in the kit can be any cardiac glycoside known in the art for treating heart failure including, but not limited to ouabain, digoxin, digitoxin, oleandrin, neriifolin, odoroside A and H, cymarin, sarmentocymarin, periplocymarin, K-strophantin, thevetin A, cerberin, peruvoside, thevetosin, thevetin B, tanghinin, deacetyltanghinin, echujin, hongheloside G, honghelin, periplocin, strophantidol, nigrescin, uzarin, calotropin, cheiroside A, cheirotoxin, euonoside, euobioside, euomonoside, lancetoxin A and B, kalanchoside, bryotoxin A-C, bryophyllin B, cotiledoside, tyledoside A-D, F and G, orbicuside A-C, alloglaucotoxin, corotoxin, coroglaucin, glaucorin, scillarene A and B, scilliroside, scilliacinoside, scilliglaucoside, scilliglaucosidin, scillirosidin, scillirubrosidin, scillirubroside, proscillaridin A, rubelin, convalloside, convallatoxin, bovoside A, glucobovoside A, bovoruboside, antiarin A, helleborin, hellebrin, adonidin, adonin, adonitoxin, thesiuside, gitoxin, gitalin, F-gitonin, digitonin, lanatoside A-C, bufotalin, bufotalinin, bufotalidin, pseudobufotalin, acetyldigitoxin, acetyl-oleandrin, beta-methyldigoxin and alpha-methyldigoxin, and combinations thereof.

The pharmaceutical compositions can, if desired, be presented in a pack or dispenser device (individually or collectively referred to as "a kit"), which can contain one or more unit dosage forms containing the active compound(s) and compositions. The kit can, for example, comprise metal or plastic foil, such as a blister pack. The kit can be accompanied by instructions for administration.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Inhibition of Mitochondrial Na+/Ca2+ Exchange Mitigates the Adverse Effects of Ouabain on Mitochondrial Energetics and Arrhythmias Overview The data provided in Example 1 demonstrate that in isolated cardiomyocytes, ouabain (plus β-adrenergic stimulation) elevated $[Na^+]_i$ in a dose-dependent way, suppressed $[Ca^{2+}]_m$ accumulation, decreased the NADH/NAD+ redox potential, and increased reactive oxygen species (ROS) level, whereas concomitant treatment with an mNCE inhibitor, e.g., CGP-37157, ameliorated these effects. CGP-37157 also attenuated cellular $Ca^{2+}$ overload, delayed afterdepolarizations (DADs), and the proarrhythmic effects of ouabain.

Further, the data provided in Example 1 demonstrate that in isolated perfused hearts, ouabain mediated positive inotropic effects, increasing left ventricular diastolic pressure (LVDP), contractility, and oxygen consumption. These positive inotropic effects were enhanced by the application of CGP-37157. β-adrenergic stimulation further increased contractility in ouabain-treated hearts and the positive inotropic effect was potentiated in the presence of CGP-37157. Furthermore, CGP-37157 reduced arrhythmia scores and markedly decreased the incidence of ventricular fibrillation.

Materials and Methods

Animal:

250- to 300-g Hartley guinea pigs were obtained from Hill Top and housed in an animal facility at the Johns Hopkins University. This study conforms to the *Guide for the Care and Use of Laboratory Animals* published by the National Institutes of Health (NIH Publication No. 85-23, revised 1996) and was approved by the Johns Hopkins Animal Care and Use Committee.

Cell Isolation:

Guinea pig ventricular myocytes were isolated by enzymatic digestion as described previously. O'Rourke, B., et al., "Oscillations of membrane current and excitability driven by metabolic oscillations in heart cells," *Science*, 265(5174): 962-966 (Aug. 12, 1994). Cells were suspended in Dulbecco's Modification of Eagle's Medium (DMEM) supplemented with 5% fetal bovine serum, 1% penicillin/streptomycin, and 15 mmol/L HEPES, pH 7.4, and stored in a 5% $CO_2$ incubator at 37° C.

Fluorescence Recording:

Cytosolic $Ca^{2+}$ ($[Ca^{2+}]_c$), mitochondrial $Ca^{2+}$ ($[Ca^{2+}]_m$), and $[Na^+]_i$ were measured with the fluorescent indicators indo-1, rhod-2, and sodium-binding benzofuran isophthalate (SBFI), respectively (Invitrogen, Carlsbad, Calif.), and mitochondrial NADH was measured as the cellular autofluorescence with 360-nm excitation/450-nm emission. Indo-1 was loaded into cell with the membrane permeable form, indo-1 AM. To minimize indo-1 loading into the mitochondrial compartment, cells were briefly incubated with indo-1 AM at room temperature for 20 min. Rhod-2 and SBFI experiments were carried out as previously described. Maack et al., supra, Liu and O'Rourke, supra. Cytoplasmic rhod-2 was eliminated by using rhod-2-free patch pipettes. Maack et al., supra, Liu and O'Rourke, supra. The ROS-sensitive fluorescent probe 5-(-6)-chloromethyl-2',7'-dichlorohydrofluorescein diacetate (CM-H2DCFDA) was used to monitor the extent of oxidative stress, as previously described. Aon, M. A., et al., "Synchronized whole cell oscillations in mitochondrial metabolism triggered by a local release of reactive oxygen species in cardiac myocytes," *J. Biol. Chem.*, 278(45):44735-44744 (Nov. 7, 2003). This probe is primarily localized in the mitochondrial matrix, see Aon et al., supra, and is oxidized by hydrogen peroxide to yield fluorescent CM-DCF, thus indirectly reporting mitochondrial superoxide production.

Protocol for Experiments in Isolated Myocytes:

Isolated ventricular myocytes were loaded into a heated field-stimulation chamber (Warner Instruments, Hamden, Conn.) at 37° C. on the stage of a fluorescence microscope (Nikon Eclipse TE300, Nikon Instruments, Inc., Melville, N.Y.). The myocytes were first superfused with control Tyrode's solution containing: NaCl (130 mmol/L), KCl (5 mmol/L), $MgCl_2$ (1 mmol/L), Na-HEPES (10 mmol/L), $CaCl_2$ (2 mmol/L), glucose (10 mmol/L), at pH 7.4. After one minute of recording in the absence of electrical stimulation in control buffer, 1-μM ouabain and 100-nM isoproterenol, with or without 1 μM CGP-37157, were added to buffer. After another five minutes of recording, myocytes were field-stimulated at 1 Hz for three minutes followed by a two-minute recording after returning to the resting state. To record $[Ca^{2+}]_m$ and action potentials, myocytes were whole-cell patch-clamped at 37° C. Tyrode's solution was used as external solution and the internal solution contained: NaCl (10 mmol/L), KCl (19 mmol/L), K-glutamate (125 mmol/L), $MgCl_2$ (0.5 mmol/L), HEPES (10 mmol/L), MgATP (5 mmol/L), at pH 7.25.

Protocol for Isolated Perfused Heart Experiments:

Guinea pig hearts were quickly excised under anesthesia and mounted on a modified Langendorff apparatus attached to a Powerlab system (AD Instruments, Colorado Springs, Colo.). Hearts were perfused with gassed (95/5% $O_2/CO_2$) control buffer containing: 118-mM NaCl, 24-mM $NaHCO_3$, 1.2-mM $KH_2PO_4$, 4.75-mM KCl, 1.2-mM $MgSO_4$, 2.0-mM $CaCl_2$, and 10-mM glucose. A buffer-filled latex balloon (Harvard apparatus) was inserted through the mitral valve into the left ventricle. Hearts were suspended in a buffer-filled heating chamber maintained at 37° C. and two electrodes were placed into the bath for volume-conducted electrocardiogram recordings. Heart rate, left ventricular developed pressure (LVDP), maximal rates of contraction and relaxation (±dP/dt), oxygen consumption, and electrocardiograms (ECG) were recorded on a computer. After a ten-minute equilibration period, hearts were subjected to the following protocol: ten-minute baseline recording while the heart was perfused with control buffer, ten-minute recording while 0.25-μM ouabain with or without 1 μM CGP-37157, and sixty-minute recording while hearts were stimulated with 25-nM isoproterenol. The measurements of hemodynamic parameters were determined by taking the average during the last two minutes before ouabain treatment (baseline) and for two minutes during the maximal effect on LVDP of either ouabain or isoproterenol.

$O_2$ Consumption:

Cardiac $O_2$ concentration was measured with an $O_2$ probe attached to a PowerLab system (AD Instruments). The probe was calibrated with 95% $O_2$-saturated buffer as 100% and 100% $N_2$-saturated buffer as 0%. The molar concentration of $O_2$ consumption was calculated from percentage concentration with the following equation:

$$VO_2(\mu mol/min/g\ dwt) = CF \times (0.02373/22.414) \times ((760-p)/760) \times (\Delta O_2\%/100)/dwt$$

where CF is coronary flow (mL/min); 0.02373 is the absorption coefficient of $O_2$ in $H_2O$ at 37° C.; 22.414 is the volume (L) of 1 mol gas at STP; 760 is 1 atm in mm Hg; p equals 47.067, which is the vapor pressure of $H_2O$ at 37° C.; $\Delta O_2\%$ is the difference in $O_2$ percentage concentration between inflow buffer collected from cannula before heart was mounted and outflow buffer collected from pulmonary artery; dwt is dry heart weight.

Assessment of Cardiac Arrhythmias:

Arrhythmias were characterized in accordance with the Lambeth Conventions, see Walker, M. J., et al., *Cardiovasc. Res.*, 22(7):447-455 (July 1988), and scores were tabulated for the ten-minute period of ouabain treatment using modified Score A as described by Curtis, M. J. and Walker, M. J., "Quantification of arrhythmias using scoring systems: an examination of seven scores in an in vivo model of regional myocardial ischaemia," *Cardiovasc. Res.*, 22(9):656-665 (September 1988). Briefly, each heart was given a score based on the following criteria: 0: <50 ventricular premature beats; 1: 50-499 ventricular premature beats; 2: >500 ventricular premature beats and/or one episode of spontaneously reverting ventricular tachycardia or ventricular fibrillation; 3: more than one episode of spontaneously reverting ventricular tachycardia or fibrillation (<2 min); 4: >2 min of ventricular tachycardia or fibrillation.

Statistical Analysis:

Data are expressed as mean±SEM. Effects of ouabain and CGP-37157 on the cytosolic $Ca^{2+}$ transient and on the arrhythmia scores were analyzed with unpaired t-tests. Effects of ouabain and isoproterenol on hemodynamics were analyzed with paired t-tests. Differences in the incidence of VF were analyzed with Fisher's Exact Test. $O_2$ consumption was analyzed with one way ANOVA.

Effect of Ouabain on $[Na^+]_i$

Application of ouabain to isolated myocytes at rest or with 1-Hz stimulation elevated $[Na^+]_i$ monotonically in a dose-dependent way. As shown in FIG. 1, 1-Hz stimulation increased the rate of $[Na^+]_i$ accumulation slightly. To optimize the conditions of the present study so that $[Na^+]_i$ could be elevated efficiently, but with acceptable toxicity during the protocol, 1-µM ouabain was used in the isolated myocyte experiments described immediately herein below.

Effects on $[Ca^{2+}]_m$ and Mitochondrial NADH During Increased Work

Elevating $[Na^+]_i$ by NKA inhibition using ouabain-decreased $[Ca^{2+}]_m$ accumulation (FIG. 2A) and resulted in net mitochondrial NADH oxidation (FIG. 2A). In ouabain-treated myocytes, the NADH level decreased significantly during 1-Hz stimulation from 81.7±1.8% before stimulation to 52.3±5.7% by the end of stimulation, whereas, in the presence of CGP-37157, the NADH level was well maintained during stimulation (78.3±3.2% before stimulation and 80.6±2.5% at the end of stimulation). Recordings of $[Ca^{2+}]_m$ in cells treated with ouabain showed that $[Ca^{2+}]_m$ increased minimally (e.g., diastolic $[Ca^{2+}]_m$ increased by <10%) during 1-Hz stimulation and that CGP-37157 significantly enhanced $[Ca^{2+}]_m$ accumulation (FIG. 2A).

The oxidation of the NADH pool during the increase in work in the presence of ouabain did not reverse after cessation of electrical stimulation. In keeping with a hypothesis that the lack of NADH recovery under high $[Na^+]_i$ conditions might be a consequence of oxidative damage, see O'Rourke, B. and Maack, C., "The role of Na dysregulation in cardiac disease and how it impacts electrophysiology," *Drug Discov. Today*, 4(4):207-217 (2007), ouabain-treated myocytes displayed higher rates of oxidation of CM-DCF; an effect further exacerbated by electrical stimulation (FIG. 3). Co-application of CGP-37157 abolished the increase in oxidative stress induced by ouabain.

Inhibition of mNCE Mitigates Ouabain-Induced Dysfunction and DAD-Triggered Action Potentials To investigate the effects of ouabain and CGP-37157 on $[Ca^{2+}]_c$ cycling, $[Ca^{2+}]_c$ was monitored with indo-1. Representative $[Ca^{2+}]_c$ recordings at the onset (FIG. 4A; left panels) and at the end (FIG. 4A; right panels) of 1-Hz stimulation in the presence of 100-nM isoproterenol revealed that ouabain increased the probability of cytosolic $Ca^{2+}$ overload and extrasystolic $Ca^{2+}$ release (FIG. 4A; OUA). In the absence of CGP-37157, ouabain treatment increased the amplitude of $[Ca^{2+}]_c$ transient ($\Delta[Ca^{2+}]_c$) by 112% compared to that of control, whereas the addition of CGP-37157 attenuated the effect of ouabain on $\Delta[Ca^{2+}]_c$, with a 74% increase compared to control (FIG. 4B). The attenuation of the $\Delta[Ca^{2+}]_c$ increase by CGP-37157 suggests that mitochondria play a role in EC coupling as a $Ca^{2+}$ sink. Although administration of ouabain did not affect diastolic $[Ca^{2+}]_c$ level significantly in myocytes in the resting state, diastolic $[Ca^{2+}]_c$ was dramatically increased when the cells were paced at 1 Hz (FIG. 4C). After three minutes of stimulation, diastolic $[Ca^{2+}]_c$ in cells treated with ouabain was 750±142 nM in contrast to 123±9 nM before stimulation. CGP-37157 reduced the accumulation of diastolic $[Ca^{2+}]_c$ (370±60 nM at the end of stimulation versus 99±14 nM before stimulation). In control cells, 1-Hz stimulation did not increase diastolic $[Ca^{2+}]_c$ (117±12 nM before stimulation and 111±7 nM at the end of stimulation). As a result of increased SR $Ca^{2+}$ loading and elevated diastolic $[Ca^{2+}]_c$, the majority of cells treated with ouabain developed spontaneous $Ca^{2+}$ oscillations, extrasystolic contractions, and eventual hypercontracture during prolonged stimulation, whereas CGP-37157 significantly reduced the incidence of discordant contractions.

In current-clamped myocytes, electrically-stimulated action potentials (APs) were recorded at 1 Hz and the probability of observing one or more delayed afterdepolarization-(DAD) triggered action potentials was determined during the last minute of stimulation. Ouabain treatment caused a significant increase in the incidence of DAD-triggered APs (FIG. 5A and FIG. 5C). In myocytes treated with ouabain plus CGP-37157, DADs were still observed occasionally, but they were of smaller amplitude than in ouabain alone (FIG. 5B), and the incidence of DAD-triggered APs was not significantly different from controls (FIG. 5C).

Effects on Cardiac Function and Oxygen Consumption

To investigate whether the impact of ouabain and CGP-37157 on NADH production had any effects on cardiac energetics and function, whole-heart studies were performed and cardiac oxygen consumption and hemodynamics were recorded. Consistent with its positive inotropic effects, application of ouabain led to a 13% (p<0.05) increase of left ventricular diastolic pressure (LVDP) compared to baseline (see Tables 1A-1B).

TABLE 1A

Hemodynamics Recorded at Baseline With or Without CGP-37157

|  | HR | LVDP | +dP/dt | −dP/dt |
|---|---|---|---|---|
| −CGP | 245.3 ± 9.0 | 94.0 ± 13.6 | 1863 ± 231 | −1780 ± 233 |
| +CGP | 239.3 ± 8.0 | 91.9 ± 10.6 | 2326 ± 303 | −1872 ± 163 |

TABLE 1B

Hemodynamics Recorded With Ouabain Treatment With or Without CGP-37157

|  | HR | LVDP | +dP/dt | −dP/dt |
|---|---|---|---|---|
| −CGP | 246.3 ± 20.3 | 106.0 ± 17.0 † | 2241 ± 376 † | −1855 ± 229 † |
| +CGP | 250.0 ± 13.4 | 100.7 ± 12.0 † | 3167 ± 481 † | −2306 ± 218 † |

TABLE 1C

Hemodynamics Recorded With Ouabain Treatment and With Isoproterenol Stimulation With or Without CGP-37157

|  | HR | LVDP | +dP/dt | −dP/dt | Incidence of VF |
|---|---|---|---|---|---|
| −CGP | 315.3 ± 25.0 † | 100.4 ± 18.3 | 3529 ± 644 † | 2820 ± 516 † | 7/8 |
| +CGP | 306.7 ± 22.8 † | 130.9 ± 18.4 † | 5530 ± 736 † * | −3518 ± 419 † | 2/7* |

In Table 1A-1C, hemodynamics of isolated perfused hearts were recorded at baseline, with ouabain treatment (1 μM), and with ouabain plus isoproterenol (100 nM) stimulation with or without CGP-37157 (1 μM). HR, heart rate; LVDP, left ventricular developed pressure; Oua: ouabain; CGP: CGP-37157; VF: ventricular fibrillation. *p<0.05 compared to group without CGP; † p<0.05 compared to baseline.

Rates of contraction and relaxation also were improved with a 20% and 4% increase of +dP/dt and −dP/dt, respectively (Tables 1A-1B). Application of ouabain with CGP-37157 mediated a similar increase of LVDP, but a much larger increase in +dP/dt (approximately 36%) and −dP/dt (approximately 23%) (Table 1B).

Compared to the level with ouabain treatment, administration of 25-nM isoproterenol further enhanced chronotropy and inotropy (Tables 1B-1C). Heart rate (HR) was increased similarly in the groups treated with isoproterenol in the absence (28% increase) or presence of CGP-37157 (23% increase). Remarkably, in the group without treatment of CGP-37157, LVDP was not increased further by isoproterenol, whereas +dP/dt and −dP/dt were increased by 57% and 52%, respectively. In the group treated with CGP-37157, LVDP was increased by 30%, and +dP/dt and −dP/dt were increased by 75% and 53%, respectively (Table 1C). Associated with the increased cardiac function, cardiac oxygen consumption increased upon administration of ouabain and isoproterenol. After ten minutes treatment of ouabain, whole-heart oxygen consumption increased by 18% and isoproterenol further increased oxygen consumption to a level 25% above baseline (FIG. 6). In keeping with the improved hemodynamic responses mentioned above, CGP-37157 also potentiated the increases in maximal oxygen consumption ($VO_2$) induced by ouabain and isoproterenol: ouabain increased $VO_2$ by 32%, while isoproterenol increased $VO_2$ by 53% compared to baseline (FIG. 6).

Effects on Arrhythmias

Figure 7:
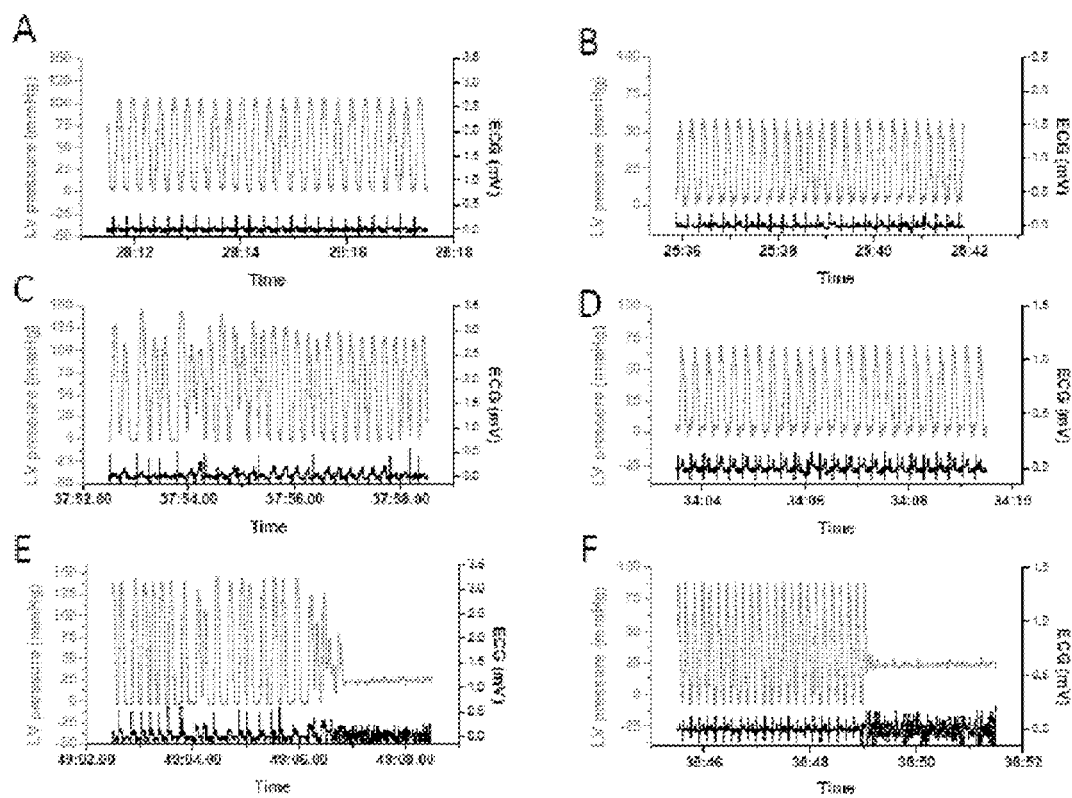

Ouabain treatment (0.25 μM) had a proarrhythmic effect in isolated perfused hearts, with an arrhythmia score of 2.7±0.5 during the ten-minute treatment (FIG. 7 and FIG. 8). This effect became exacerbated after administration of isoproterenol: ventricular fibrillation (VF) occurred in 7 out of 8 hearts (Table 1C). Treatment with CGP-37157, however, significantly attenuated the pro-arrhythmic effects of ouabain. The arrhythmia score during ten-minute ouabain treatment was reduced to 1.1±0.4 (FIG. 8) and the incidence of VF also significantly decreased (2 out of 7 hearts, p<0.05) (Table 1C).

Without wishing to be bound to any one particular theory, in view of the results disclosed hereinabove, the presently disclosed subject matter describes the mechanisms underlying the adverse effects of ouabain on mitochondrial energetics. More particularly, the presently disclosed subject matter demonstrates that ouabain treatment impairs NADH production in isolated myocytes as a consequence of cytosolic $Na^+$ loading, and this effect was prevented by CGP-37157. In isolated myocytes, CGP-37157 was shown to (A) enhance mitochondrial $Ca^{2+}$ uptake in the presence of ouabain; (B) decrease cytosolic diastolic $Ca^{2+}$ overload, blunting spontaneous $Ca^{2+}$ release, and (C) decrease the incidence of DAD-triggered action potentials. At the whole-heart level, CGP-37157 prevented the ouabain-induced impairment of mitochondrial energetics, wherein such impairment limits the positive inotropic effects of both ouabain and isoproterenol. Moreover, improved contractility with CGP-37157 treatment correlated with increased rates of mitochondrial respiration. Consistently, CGP-37157 attenuated ouabain-induced arrhythmias in perfused hearts and significantly decreased the incidence of VF.

The Effects of Ouabain on Cardiac Energetics

Previous studies showed that elevated $[Na^+]_i$ impairs mitochondrial NADH production by blunting $[Ca^{2+}]_m$ accumulation during increased work, and that partial inhibition of mNCE by CGP-37157 restores $[Ca^{2+}]_m$ accumulation and NADH production. Maack et al., supra, Liu and O'Rourke, supra. The presently disclosed subject matter investigated whether the known toxicity of digitalis therapy might involve impairment of cardiac energetics, and if inhibition of mNCE could abrogate this negative effect. More particularly, the presently disclosed subject matter examined the effects of ouabain and CGP-37157 on NADH production in isolated myocytes, and $O_2$ consumption and cardiac performance in whole heart.

In isolated cardiac myocytes, the elevation of $[Na^+]_i$ induced by NKA inhibition with ouabain significantly oxidized the mitochondrial NADH pool, which was well maintained in the presence of CGP-37157. In intact perfused hearts, CGP-37157 enhanced the positive inotropic effects of both ouabain and isoproterenol, and increased the maximal $VO_2$ response. The additive effect of CGP-37157 indicates that ouabain's positive effects on $Ca^{2+}$ cycling and contractility are limited by a mismatch of energy supply and demand. Impairment of mitochondrial NADH balance led to $Ca^{2+}$ dysregulation and the triggering of spontaneous SR $Ca^{2+}$ release and DAD-triggered APs in cardiomyocytes. These effects are mediated by elevated $[Na^+]_i$ and depressed $[Ca^{2+}]_m$ accumulation because CGP-37157 restored the $[Ca^{2+}]_m$ response, maintained the $NAD^+$/NADH redox potential during increased work, and enhanced the whole-heart respiration rate.

It was previously demonstrated that if $[Ca^{2+}]_m$ accumulation during an increase in work does not reach a critical threshold level, then there is a linear correlation between $[Ca^{2+}]_m$ and NADH level. In other words, more oxidation of the NADH pool occurs when the mitochondrial $Ca^{2+}$ signal is insufficient to stimulate NADH production. This limitation can be overcome through several interventions, such as decreasing cytoplasmic $Na^+$, increasing cytosolic inorganic phosphate concentration, enhancing mitochondrial $Ca^{2+}$ uptake with β-adrenergic stimulation or increased extracellular $Ca^{2+}$, or partially inhibiting mNCE. Maack et al., supra. In the whole heart, isoproterenol can facilitate $[Ca^{2+}]m$ uptake, both by increasing heart rate and by enhancing SR $Ca^{2+}$ cycling; however, the presently disclosed subject matter shows that when $[Na^+]_i$ is high as a result of ouabain treatment, even the β-adrenergic response is limited. This limitation can be overcome by improving $[Ca^{2+}]_m$ accumulation with CGP-37157, as evidenced by an increased positive inotropic effect and enhanced $VO_2$ max.

Effects of CGP37157 on Ouabain-Induced Arrhythmias

Figure 4:
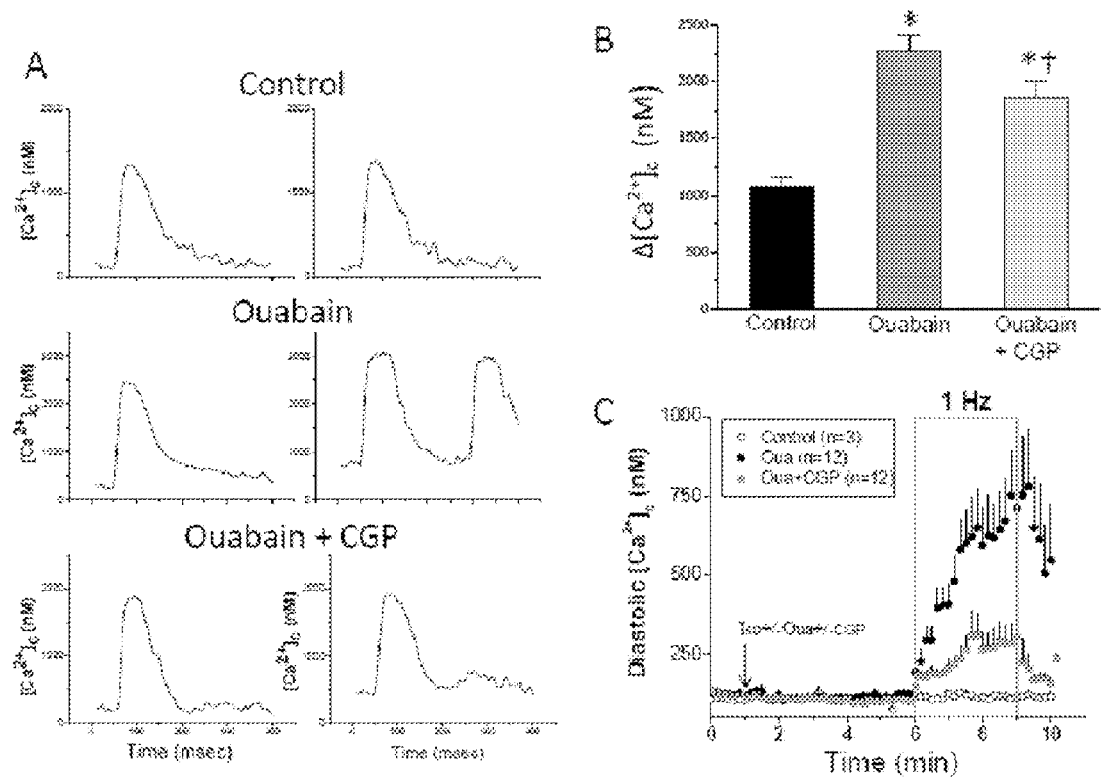

Cardiac arrhythmias are one of the major adverse effects of cardiac glycosides in clinical use. The mechanisms underlying the arrhythmogenic effect are incompletely understood, but are thought to involve $Ca^{2+}$-triggered events, occurring as a consequence of NKA inhibition and SR $Ca^{2+}$ overload. Trafford, A. W., et al., "Factors affecting the propagation of locally activated systolic Ca transients in rat ventricular myocytes," *Pflugers Arch.*, 425(1-2):181-183 (October 1993); Lukyanenko V., et al., "The role of luminal $Ca^{2+}$ in the generation of $Ca^{2+}$ waves in rat ventricular myocytes," *J. Physiol.*, 518 (Pt. 1):173-186 (Jul. 1, 1999). As SR $Ca^{2+}$ load rises, the open probability of RyR receptor increases and uncontrolled SR $Ca^{2+}$ release may be initiated, promoting arrhythmogenic electrical signals including early- or delayed-afterdepolarizations (EADs or DADs). Discordant $Ca^{2+}$ release was observed in the presence of ouabain, along with an excessive increase in diastolic $Ca^{2+}$ (FIG. 4). Both of these effects were attenuated by CGP-37157, supporting the idea that mitochondria fulfill multiple roles in the integrated physiology of the cell, including buffering $[Ca^{2+}]_c$ during inotropic stimuli, producing ATP to support normal $Ca^{2+}$ cycling, and modulating the redox status of the cardiomyocyte. Although the subject of some debate, O'Rourke, B. and Blatter, L. A., "Mitochondrial Ca(2+) uptake: Tortoise or hare?" *J. Mol. Cell. Cardiol.*, 46(6), 767-774 (June 2009), evidence exists that mitochondria sequester $[Ca^{2+}]_c$ during EC coupling on a beat-to-beat basis. Maack et al., supra; Bell, C. J., et al., "ATP regulation in adult rat cardiomyocytes: time-resolved decoding of rapid mitochondrial calcium spiking imaged with targeted photoproteins,"*J. Biol. Chem.*, 281 (38):28058-28067 (Sep. 22, 2006); Robert, V., et al., "Beat-to-beat oscillations of mitochondrial $[Ca^{2+}]$ in cardiac cells," *Embo J.* 20(17):4998-5007 (Sep. 3, 2001); Seguchi, H., et al., "Propagation of $Ca^{2+}$ release in cardiac myocytes: role of mitochondria," *Cell Calcium* 38(1):1-9 (July 2005); Trollinger, D. R., et al., "Mitochondrial calcium transients in adult rabbit cardiac myocytes: inhibition by ruthenium red and artifacts caused by lysosomal loading of Ca(2+)-indicating fluorophores,"*Biophys J.* 79(1):39-50 (July 2000).

The $Ca^{2+}$ transient is increased when the mitochondrial $Ca^{2+}$ uniporter is blocked, Maack et al., supra; Seguchi et al., supra, and decreased when mNCE is inhibited. Maack et al., supra. In addition to the direct effect of mitochondrial $Ca^{2+}$ dynamics on intracellular $Ca^{2+}$ fluxes, mitochondria also appear to influence the propagation of $Ca^{2+}$ waves. Boitier, E. et al., "Mitochondria exert a negative feedback on the propagation of intracellular $Ca^{2+}$ waves in rat cortical astrocytes,"*J. Cell. Biol.* 145(4):795-808 (May 17, 1999), demonstrated that when mitochondrial $Ca^{2+}$ uptake was prevented by mitochondrial depolarization, the rate of propagation of $Ca^{2+}$ wave was significantly increased in astrocytes. Similarly, Seguchi et al., supra, inhibited mitochondrial $Ca^{2+}$ uptake with Ru360 and converted non-propagating $Ca^{2+}$ release into a propagating release in isolated ventricular myocytes. Therefore, CGP-37157 might have an anti-arrhythmic effect because it attenuates SR $Ca^{2+}$ overload and inhibits uncontrolled propagation of local $Ca^{2+}$ release events. Alternatively, the suppression of DAD-triggered APs and arrhythmias by CGP-37157 may be related to the reduced level of oxidative stress when mitochondrial function is preserved (FIG. 3). In whole hearts, this beneficial effect of CGP-37157 was manifested as a decreased incidence of ouabain-induced arrhythmias, and, importantly, the presently disclosed subject matter also demonstrated that the progression to ventricular fibrillation by isoproterenol was suppressed by CGP-37157.

Summary

Cardiac glycosides have played an important role in the treatment of HF for over two hundred years. The use of cardiac glycosides in HF has declined in the past decade. Adams, K. F., Jr., et al., "Characteristics and outcomes of patients hospitalized for heart failure in the United States: rationale, design, and preliminary observations from the first 100,000 cases in the Acute Decompensated Heart Failure National Registry (ADHERE),"*Am. Heart* 149(2):209-216 (February 2005). One potential reason for this decline could be the lack of mortality benefit of digoxin as suggested by the Digoxin Investigation Group (DIG) trial. The Digitalis Investigation Group, "The effect of digoxin on mortality and morbidity in patients with heart failure," *N. Engl. J. Med.* 336(8): 525-533 (Feb. 20, 1997). In the DIG trial, it appeared that digoxin therapy did not affect overall mortality in HF patients although, like other studies, see Packer, M., et al., "Withdrawal of digoxin from patients with chronic heart failure treated with angiotensin-converting-enzyme inhibitors. RADIANCE Study," *N. Engl. J. Med.*, 329(1):1-7 (Jul. 1, 1993); Uretsky, B. F., et al., "Randomized study assessing the effect of digoxin withdrawal in patients with mild to moderate chronic congestive heart failure: results of the PROVED trial. PROVED Investigative Group," *J. Am. Coll. Cardiol.*, 22(4): 955-962 (October 1993), it improved HF symptoms and reduced hospitalization rates due to worsening HF. The Digitalis Investigation Group, supra.

The improvement of cardiac function without benefit to mortality could be partially explained by an obvious increase of cardiac sudden death in patients treated with digoxin. By considering serum digoxin concentration (SDC) as a factor, a recent post hoc analysis of the DIG trail demonstrated that digoxin therapy reduced mortality of all HF patients with a SDC of 0.5-0.9 ng/mL, whereas, at higher SDC (≥1.0 ng/mL), digoxin therapy reduced hospitalizations with no effect on mortality. Ahmed, A., et al., "Digoxin and reduction in mortality and hospitalization in heart failure: a comprehensive post hoc analysis of the DIG trial," *Eur. Heart* 1, 27(2): 178-186 (January 2006). This analysis suggests that, as SDC increases, the beneficial effects of digoxin on mortality could be offset by increased incidence of arrhythmias and sudden death. The beneficial effects of CGP-37157 on arrhythmias and VF displayed in the presently disclosed subject matter support a therapeutic strategy to improve cardiac glycoside treatment of patients in HF with combination therapy designed to inhibit both the NKA and the mNCE.

In this regard, it has been previously shown that elevated $[Na^+]_i$ in myocytes isolated from failing hearts impaired mitochondrial energetics during increased work. Liu and O'Rourke, supra. Although digoxin therapy has been shown to increase cardiac contractility, exercise time, and $O_2$ consumption of HF patients in clinical trials (reviewed in Rahimtoola, supra), the adverse effect of elevated $[Na^+]_i$ already present in HF could be intensified with digoxin treatment. The presently disclosed subject matter suggests that enhancement of $[Ca^{2+}]_m$ could further improve cardiac function by digoxin therapy. Digoxin therapy is not the only source of glycoside that affects HF patients. Various endogenous digitalis-like compounds have been identified in human and animals, and their concentrations vary in different disease conditions (for review, see Bagrov, A. Y. and Shapiro, J. I., "Endogenous digitalis: pathophysiologic roles and therapeutic applications," *Nat. Clin. Pract. Nephrol.*, 4(7):378-392 (July 2008). In 1991, Hamlyn, J. M., et al., "Identification and characterization of an ouabain-like compound from human plasma," *Proc. Natl. Acad. Sci. USA*. 88(14):6259-6263 (Jul. 15, 1991), identified endogenous ouabain in human plasma, which is structurally, biologically, and immunologically indistinguishable from plant-derived ouabain.

The plasma level of endogenous ouabain was then evaluated in HF patients and the result indicated a significant increase in endogenous ouabain in HF patient compared to normal controls. Gottlieb, S. S., et al., "Elevated concentrations of endogenous ouabain in patients with congestive heart failure," *Circulation* 86(2):420-425 (August 1992). Using an animal model, Fedorova, O. V., et al., "Coordinated shifts in Na/K-ATPase isoforms and their endogenous ligands during cardiac hypertrophy and failure in NaCl-sensitive hypertension," *J. Hypertens.*, 22(2):389-397 (February 2004), found that plasma levels of endogenous ouabain did not change in the stage of hypertrophy, but was substantially increased by threefold in the transition to heart failure. These studies indicated that the adverse effects of cardiac glycosides on cardiac energetics and arrhythmias also may exist in HF patients who are not receiving digoxin.

In summary, the presently disclosed subject matter demonstrates that ouabain-induced elevation of $[Na^+]_i$ has an adverse effect on mitochondrial energetics, and CGP-37157 abrogates the negative effect on energetics and attenuates ouabain-induced arrhythmias. Further, the presently disclosed methods overcome one of the limitations of an approved strategy for treating heart failure by targeting a mitochondrial protein that has been heretofore unrecognized as a downstream contributor to the toxicity of cardiac glycosides. Accordingly, the presently disclosed subject matter provides a potential therapeutic strategy to improve digoxin's positive effects while reducing the risk of digoxin toxicity.

Example 2

Prevention of Sudden Cardiac Death and Contractile Decompensation in Heart Failure by Inhibition of the Mitochondrial Sodium-Calcium Exchanger (mNCE)

As provided herein, the presently disclosed subject matter investigated whether these mechanisms underlie sudden cardiac death (SCD) and contractile decompensation in hypertrophic heart failure in two novel guinea-pig models of combined ascending aortic constriction together with β-adrenergic stimulation and whether therapy via mNCE inhibition was effective. Accordingly, in some embodiments, the presently disclosed subject matter provides a therapeutic strategy for treating heart failure.

Two models were developed: acute SCD and delayed SCD. The acute SCD model used a high dose of isoproterenol (5 mg/kg) administered by a single intraperitoneal injection two days after ascending aortic banding; and the delayed SCD model used low dose isoproterenol (week one: 1 mg/kg; subsequent weeks: 2 mg/kg), administered by daily intraperitoneal injection over the course of five weeks after aortic banding. Additionally, a therapeutic regime comprised of chronic treatment with an inhibitor of mNCE, e.g., CGP-37157, mean dose approximately 40 µg/kg, administered by implantation of an osmotic pump in the abdominal cavity (delivery rate: 0.015 mg/kg/hr) for extended delivery of the compound was initiated.

An enhanced susceptibility to β-adrenergic receptor stimulation-related arrhythmias and sudden cardiac death was observed in the aortic-banded animals, which was ameliorated by concomitant CGP-37157 treatment. Two days after the aortic banding surgery, a single dose of 5 mg/kg isoproterenol administration (acute SCD model) resulted in a 77% death rate in the group of animals without CGP-37157 treatment, whereas with CGP-37157 treatment, the death rate decreased to 20%, ρ=0.01 (see FIG. 9).

The delayed SCD protocol was used to investigate the effect of chronic CGP-37157 treatment on mortality and the development of heart failure. Survival was extended using this protocol as compared with the acute SCD model. In the absence of CGP-37157, however, the death rate of the animals approached 60% by 30 days post-banding (see FIG. 10). In contrast, more than 78% of the animals survived in the group with CGP-37157 treatment (see FIG. 10).

Further, echocardiographic studies were carried out before surgery and at four weeks after aortic banding (see FIG. 11). Measurements of left ventricular wall thickness indicated that wall thickness was increased similarly in both groups of animals, regardless of CGP-37157 treatment (see FIG. 11, left panel). In the group with CGP-37157 treatment, however, cardiac function was maintained. Fractional Shortening (FS) was increased from 54.0%±1.0 at baseline to 59.2%±1.8 (n=6) in the CGP-37157-treated group, whereas in the absence of CGP-37157, FS was decreased from 54.9%±1.0 at baseline to 42.5%±2.8 (n=7) (see FIG. 11, right panel).

All publications, patent applications, patents, and other references mentioned in the specification are indicative of the level of those skilled in the art to which the presently disclosed subject matter pertains. All publications, patent applications, patents, and other references are incorporated herein by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Hunt S. A., Abraham W. T., Chin M. H., Feldman A. M., Francis G. S., Ganiats T. G., Jessup M., Konstam M. A., Mancini D. M., Michl K., Oates J. A., Rahko P. S., Silver M. A., Stevenson L. W., Yancy C. W., Antman E. M., Smith S. C., Jr., Adams C. D., Anderson J. L., Faxon D. P., Fuster V., Halperin J. L., Hiratzka L. F., Jacobs A. K., Nishimura R., Ornato J. P., Page R. L., Riegel B., ACC/AHA 2005 Guideline Update for the Diagnosis and Management of Chronic Heart Failure in the Adult: a report of the American College of Cardiology/American Heart Association Task Force on Practice Guidelines (Writing Committee to Update the 2001 Guidelines for the Evaluation and Management of Heart Failure): developed in collaboration with the American College of Chest Physicians and the International Society for Heart and Lung Transplantation: endorsed by the Heart Rhythm Society. *Circulation*. Sep. 20 2005; 112(12):e154-235.

Rahimtoola S. H., Digitalis therapy for patients in clinical heart failure. *Circulation*. Jun. 22 2004; 109(24):2942-2946.

Gheorghiade M., Adams K. F., Jr., Colucci W. S., Digoxin in the management of cardiovascular disorders. *Circulation*. Jun. 22 2004; 109(24):2959-2964.

Ribner H. S., Plucinski D. A., Hsieh A. M., Bresnahan D., Molteni A., Askenazi J., Lesch M., Acute effects of digoxin on total systemic vascular resistance in congestive heart failure due to dilated cardiomyopathy: a hemodynamic-hormonal study. *Am. J. Cardiol.*, Nov. 15 1985; 56(13): 896-904.

van Veldhuisen D. J., Man in't Veld A. J., Dunselman P. H., Lok D. J., Dohmen H. J., Poortermans J. C., Withagen A. J., Pasteuning W. H., Brouwer J., Lie K. I., Double-blind placebo-controlled study of ibopamine and digoxin in patients with mild to moderate heart failure: results of the Dutch Ibopamine Multicenter Trial (DIMT). *Journal of the American College of Cardiology*. Nov. 15 1993; 22(6): 1564-1573.

Alicandri C., Fariello R., Boni E., Zaninelli A., Castellano M., Beschi M., Agabiti Rosei E., Muiesan G., Captopril versus digoxin in mild-moderate chronic heart failure: a crossover study. *J. Cardiovasc. Pharmacol.* 1987; 9 Suppl 2:S61-67.

Covit A. B., Schaer G. L., Sealey J. E., Laragh J. H., Cody R. J., Suppression of the renin-angiotensin system by intravenous digoxin in chronic congestive heart failure. *The American journal of medicine*. September 1983; 75(3): 445-447.

Maack C., Cortassa S., Aon M. A., Ganesan A. N., Liu T., O'Rourke B., Elevated cytosolic $Na^+$ decreases mitochondrial $Ca^{2+}$ uptake during excitation-contraction coupling and impairs energetic adaptation in cardiac myocytes. *Circulation research*. Jul. 21 2006; 99(2):172-182.

Liu T., O'Rourke B., Enhancing mitochondrial $Ca^{2+}$ uptake in myocytes from failing hearts restores energy supply and demand matching. *Circulation research*. Aug. 1 2008; 103(3):279-288.

McCormack J. G., Halestrap A. P., Denton R. M., Role of calcium ions in regulation of mammalian intramitochondrial metabolism. *Physiological reviews*. April 1990; 70(2):391-425.

O'Rourke B., Ramza B. M., Marban E., Oscillations of membrane current and excitability driven by metabolic oscillations in heart cells. *Science* (New York, N.Y. Aug. 12 1994; 265(5174):962-966.

Aon M. A., Cortassa S., Marban E., O'Rourke B., Synchronized whole cell oscillations in mitochondrial metabolism triggered by a local release of reactive oxygen species in cardiac myocytes. *J Biol. Chem.* Nov. 7 2003; 278(45): 44735-44744.

Walker M. J., Curtis M. J., Hearse D. J., Campbell R. W., Jame M. J., Yellon D. M., Cobbe S. M., Coker S. J., Harness J. B., Harron D. W., et al. The Lambeth Conventions: guidelines for the study of arrhythmias in ischaemia infarction, and reperfusion. *Cardiovascular research*. July 1988; 22(7): 447-455.

Curtis M. J., Walker M. J., Quantification of arrhythmias using scoring systems: an examination of seven scores in an in vivo model of regional myocardial ischaemia. *Cardiovascular research*. September 1988; 22(9):656-665.

O'Rourke B., Maack C., The role of Na dysregulation in cardiac disease and how it impacts electrophysiology. *Drug discovery today.* 2007; 4(4):207-217.

Trafford A. W., O'Neill S. C., Eisner D. A., Factors affecting the propagation of locally activated systolic Ca transients in rat ventricular myocytes. *Pflugers Arch*. October 1993; 425(1-2):181-183.

Lukyanenko V., Subramanian S., Gyorke I., Wiesner T. F., Gyorke S., The role of luminal $Ca^{2+}$ in the generation of $Ca^{2+}$ waves in rat ventricular myocytes. *J Physiol*. Jul. 1 1999; 518 (Pt 1):173-186.

O'Rourke B., Blatter L. A., Mitochondrial Ca(2+) uptake: Tortoise or hare? *Journal of molecular and cellular cardiology*. Dec. 31 2008.

Bell C. J., Bright N. A., Rutter G. A., Griffiths E. J., ATP regulation in adult rat cardiomyocytes: time-resolved decoding of rapid mitochondrial calcium spiking imaged with targeted photoproteins. *J Biol. Chem*. Sep. 22 2006; 281(38):28058-28067.

Robert V., Gurlini P., Tosello V., Nagai T., Miyawaki A., Di Lisa F., Pozzan T., Beat-to-beat oscillations of mitochondrial $[Ca^{2+}]$ in cardiac cells. *Embo J* Sep. 3 2001; 20(17): 4998-5007.

Seguchi H., Ritter M., Shizukuishi M., Ishida H., Chokoh G., Nakazawa H., Spitzer K. W., Barry W. H., Propagation of $Ca^{2+}$ release in cardiac myocytes: role of mitochondria. *Cell Calcium*. July 2005; 38(1):1-9.

Trollinger D. R., Cascio W. E., Lemasters J. J., Mitochondrial calcium transients in adult rabbit cardiac myocytes: inhibition by ruthenium red and artifacts caused by lysosomal loading of Ca(2+)-indicating fluorophores. *Biophys J*. July 2000; 79(1):39-50.

Boitier E., Rea R., Duchen M. R., Mitochondria exert a negative feedback on the propagation of intracellular $Ca^{2+}$ waves in rat cortical astrocytes. *J. Cell Biol*. May 17, 1999; 145(4):795-808.

Adams K. F., Jr., Fonarow G. C., Emerman C. L., LeJemtel T. H., Costanzo M. R., Abraham W. T., Berkowitz R. L., Galvao M., Horton D. P., Characteristics and outcomes of patients hospitalized for heart failure in the United States: rationale, design, and preliminary observations from the first 100,000 cases in the Acute Decompensated Heart Failure National Registry (ADHERE). *Am Heart J*. February 2005; 149(2):209-216.

The effect of digoxin on mortality and morbidity in patients with heart failure. The Digitalis Investigation Group. *N Engl J Med*. Feb. 20 1997; 336(8):525-533.

Packer M., Gheorghiade M., Young J. B., Costantini P. J., Adams K. F., Cody R. J., Smith L. K., Van Voorhees L., Gourley L. A., Jolly M. K., Withdrawal of digoxin from patients with chronic heart failure treated with angiotensin-converting-enzyme inhibitors. RADIANCE Study. *N Engl J Med*. Jul. 1 1993; 329(1):1-7.

Uretsky B. F., Young J. B., Shahidi F. E., Yellen L. G., Harrison M. C., Jolly M. K., Randomized study assessing the effect of digoxin withdrawal in patients with mild to moderate chronic congestive heart failure: results of the PROVED trial. PROVED Investigative Group. *J Am Coll Cardiol*. October 1993; 22(4):955-962.

Ahmed A., Rich M. W., Love T. E., Lloyd-Jones D. M., Aban L B., Colucci W. S., Adams K. F., Gheorghiade M., Digoxin and reduction in mortality and hospitalization in heart failure: a comprehensive post hoc analysis of the DIG trial. *Eur Heart J*. January 2006; 27(2):178-186.

Bagrov A. Y., Shapiro J. I., Endogenous digitalis: pathophysiologic roles and therapeutic applications. *Nat Clin Pract Nephrol*. July 2008; 4(7):378-392.

Hamlyn J. M., Blaustein M. P., Bova S., DuCharme D. W., Harris D. W., Mandel F., Mathews W. R., Ludens J. H., Identification and characterization of a ouabain-like compound from human plasma. *Proc Natl Acad Sci USA*. Jul. 15 1991; 88(14):6259-6263.

Gottlieb S. S., Rogowski A. C., Weinberg M., Krichten C. M., Hamilton B. P., Hamlyn J. M., Elevated concentrations of endogenous ouabain in patients with congestive heart failure. *Circulation*. August 1992; 86(2):420-425.

Fedorova O. V., Talan M. I., Agalakova N. I., Lakatta E. G., Bagrov A. Y., Coordinated shifts in Na/K-ATPase isoforms and their endogenous ligands during cardiac hypertrophy and failure in NaCl-sensitive hypertension. *J Hypertens*. February 2004; 22(2):389-397.

Mekhail T., et al., "Phase 1 trial of Anvirzel™ in patients with refractory solid tumors," Invest. New Drugs 24: 423-427 (2006).

U.S. Patent Application Publication No. US2004/0082521 A1, to Singh, for Novel Formulations of Digitalis Glycosides for Treating Cell-Proliferative and Other Diseases, published Apr. 29, 2004.

U.S. Patent Application Publication No. US2002/0082193 A1, to Anderson et al., for Inhibition of Mitochondrial Calcium/Sodium Antiporter, published Jun. 27, 2002.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for ameliorating or reducing the severity of an adverse effect of a cardiac glycoside in a subject being treated with the cardiac glycoside for one or more conditions or symptoms associated with heart failure, the method comprising administering to the subject a therapeutically effective amount of a mitochondrial sodium-calcium exchanger (mNCE) inhibitor, wherein the mNCE inhibitor comprises a compound of Formula I:

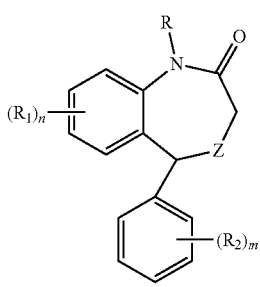

(I)

wherein:

m and n are the same or different and are integers independently selected from the group consisting of 0, 1, 2, 3, and 4;

Z is selected from the group consisting of O, S, and S(=O);

R is selected from the group consisting of H, alkyl, and substituted alkyl;

$R_1$ and $R_2$ are the same or different and at each occurrence are independently selected from the group consisting of halogen, alkyl, substituted alkyl, and nitro; or stereoisomers, prodrugs, or pharmaceutically acceptable salts thereof.

2. The method of claim 1, wherein the mNCE inhibitor is CGP-37157 and the compound of Formula I has the following structure:

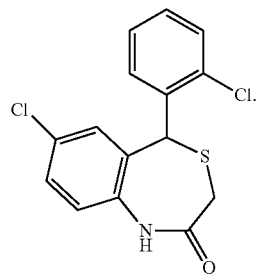 [SMILES: O=C1CSC(c2ccccc2Cl)c2cc(Cl)ccc2N1]

3. The method of claim 1, wherein the cardiac glycoside is selected from the group consisting of ouabain, digoxin, digitoxin, oleandrin, neriifolin, odoroside A and H, cymarin, sarmentocymarin, periplocymarin, K-strophantin, thevetin A, cerberin, peruvoside, thevetosin, thevetin B, tanghinin, deacetyltanghinin, echujin, hongheloside G, honghelin, periplocin, strophantidol, nigrescin, uzarin, calotropin, cheiroside A, cheirotoxin, euonoside, euobioside, euomonoside, lancetoxin A and B, kalanchoside, bryotoxin A-C, bryophyllin B, cotiledoside, tyledoside A-D, F and G, orbicuside A-C, alloglaucotoxin, corotoxin, coroglaucin, glaucorin, scillarene A and B, scilliroside, scilliacinoside, scilliglaucoside, scilliglaucosidin, scillirosidin, scillirubrosidin, scillirubroside, proscillaridin A, rubelin, convalloside, convallatoxin, bovoside A, glucobovoside A, bovoruboside, antiarin A, helleborin, hellebrin, adonidin, adonin, adonitoxin, thesiuside, gitoxin, gitalin, F-gitonin, digitonin, lanatoside A-C, bufotalin, bufotalinin, bufotalidin, pseudobufotalin, acetyldigitoxin, acetyl-oleandrin, beta-methyldigoxin and alpha-methyldigoxin, and combinations thereof.

4. The method of claim 1, wherein the adverse effect is an increase in one or more symptoms selected from the group consisting of arrhythmia, proarrythmia, delayed afterdepolarizations (DADs), ventricular fibrillation, cardiac cell injury, cardiac cell toxicity, conduction disturbance, atrioventricular block, atrial tachycardia, junctional tachycardia, ventricular premature contraction, ventricular tachycardia, nausea, vomiting, diarrhea, anorexia, blurred vision, headache, weakness, apathy and psychosis.

5. The method of claim 1, wherein the adverse effect is a detrimental change in one or more physiological characteristics of a cardiomyocyte of the subject being treated with a cardiac glycoside, wherein the detrimental change in the one or more physiological characteristics of a cardiomyocyte is selected from the group consisting of an elevated $[Na^+]_i$; a suppressed $[Ca^{2+}]_m$ accumulation; a decreased $NADH/NAD^+$ redox potential; an increased reactive oxygen species (ROS) level; and combinations thereof.

6. The method of claim 1, wherein the method enhances a positive inotropic effect of the cardiac glycoside.

7. The method of claim 1, wherein the method enhances one or more hemodynamic parameters of the subject being treated with a cardiac glycoside, wherein the hemodynamic parameter is selected from the group consisting of: an increase in left ventricular developed pressure (LVDP); an increase in contractility, an increase in the rate of contraction (+dP/dt); an increase in the rate of relaxation (−dP/dt); and combinations thereof.

8. The method of claim 1, wherein the method improves or increases oxygen consumption ($VO_2$).

9. The method of claim 1, wherein the mNCE inhibitor increases or enhances one or more physiological conditions of a cardiomyocyte of the subject, wherein the one or more physiological conditions is selected from the group consisting of mitochondrial $[Ca^{2+}]_m$ accumulation, mitochondrial NADH production, mitochondrial $[Ca^{2+}]_m$ retention capacity, and reduction of cellular oxidative stress.

10. The method of claim 1, wherein the mNCE inhibitor inhibits, decreases or attenuates one or more physiological conditions of a cardiomyocyte of the subject, wherein the one or more physiological conditions is selected from the group consisting of $[Ca^{2+}]_m$ efflux, cytosolic $[Ca^{2+}]_c$ cycling, accumulation of diastolic $[Ca^{2+}]_c$, incidence of discordant contractions, and $Ca^{2+}$ release.

11. A method for treating heart failure, the method comprising administering to a subject having or suspected of having heart failure, a therapeutically effective amount of one or more cardiac glycosides and a therapeutically effective amount of a mitochondrial sodium-calcium exchanger (mNCE) inhibitor, wherein the mNCE inhibitor comprises a compound of Formula I:

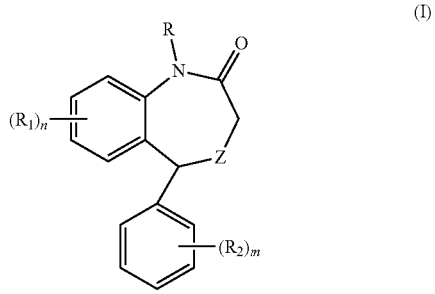

(I)

wherein:
m and n are the same or different and are integers independently selected from the group consisting of 0, 1, 2, 3, and 4;
Z is selected from the group consisting of O, S, and S(=O);
R is selected from the group consisting of H, alkyl, and substituted alkyl;
$R_1$ and $R_2$ are the same or different and at each occurrence are independently selected from the group consisting of halogen, alkyl, substituted alkyl, and nitro; or stereoisomers, prodrugs, or pharmaceutically acceptable salts thereof.

12. The method of claim 11, wherein the mNCE inhibitor is CGP-37157 and the compound of Formula I has the following structure:

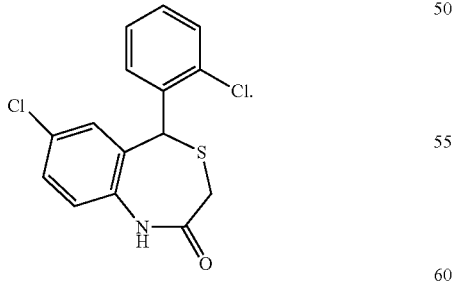

13. The method of claim 11, wherein the cardiac glycoside is selected from the group consisting of ouabain, digoxin, digitoxin, oleandrin, neriifolin, odoroside A and H, cymarin, sarmentocymarin, periplocymarin, K-strophantin, thevetin A, cerberin, peruvoside, thevetosin, thevetin B, tanghinin, deacetyltanghinin, echujin, hongheloside G, honghelin, periplocin, strophantidol, nigrescin, uzarin, calotropin, cheiroside A, cheirotoxin, euonoside, euobioside, euomonoside, lancetoxin A and B, kalanchoside, bryotoxin A-C, bryophyllin B, cotiledoside, tyledoside A-D, F and G, orbicuside A-C, alloglaucotoxin, corotoxin, coroglaucin, glaucorin, scillarene A and B, scilliroside, scilliacinoside, scilliglaucoside, scilliglaucosidin, scillirosidin, scillirubrosidin, scillirubroside, proscillaridin A, rubelin, convalloside, convallatoxin, bovoside A, glucobovoside A, bovoruboside, antiarin A, helleborin, hellebrin, adonidin, adonin, adonitoxin, thesiuside, gitoxin, gitalin, F-gitonin, digitonin, lanatoside A-C, bufotalin, bufotalinin, bufotalidin, pseudobufotalin, acetyldigitoxin, acetyl-oleandrin, beta-methyldigoxin and alpha-methyldigoxin, and combinations thereof.

14. A method for treating heart failure, the method comprising administering to a subject having or suspected of having heart failure, a therapeutically effective amount of a mitochondrial sodium-calcium exchanger (mNCE) inhibitor, wherein the mNCE inhibitor comprises a compound of Formula I:

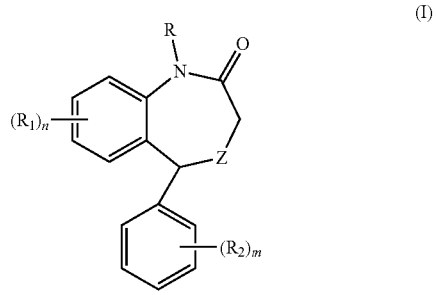

(I)

wherein:
m and n are the same or different and are integers independently selected from the group consisting of 0, 1, 2, 3, and 4;
Z is selected from the group consisting of O, S, and S(=O);
R is selected from the group consisting of H, alkyl, and substituted alkyl;
$R_1$ and $R_2$ are the same or different and at each occurrence are independently selected from the group consisting of halogen, alkyl, substituted alkyl, and nitro; or stereoisomers, prodrugs, or pharmaceutically acceptable salts thereof.

15. The method of claim 14, wherein the mNCE inhibitor is CGP-37157 and the compound of Formula I has the following structure:

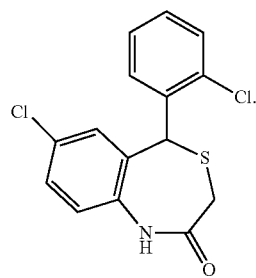 [SMILES: O=C1CSC(c2ccccc2Cl)c2cc(Cl)ccc2N1]

16. The method of claim 14, wherein the treating is ameliorating or improving one or more conditions or symptoms associated with heart failure, wherein the one or more conditions or symptoms associated with heart failure are selected from the group consisting of sudden cardiac death, contractile decompensation, fractional shortening (FS), proarrhythmia, arrhythmia, delayed afterdepolarizations (DADs), ventricular fibrillation, cardiac cell injury, cardiac cell toxicity, conduction disturbance, atrioventricular block, atrial tachycardia, junctional tachycardia, ventricular premature contraction, ventricular tachycardia, nausea, vomiting, diarrhea, anorexia, blurred vision, headache, weakness, apathy, psychosis, and combinations thereof.

17. The method of claim 14, wherein the method ameliorates or improves an ancillary symptom of heart failure, wherein the ancillary symptom of heart failure is selected from the group consisting of dyspnea, persistent coughing or wheezing, tissue edema, fatigue, lack of appetite, nausea, confusion, impaired thinking, and combinations thereof.

18. The method of claim 14, wherein the heart failure is selected from the group consisting of chronic heart failure, hypertrophic heart failure, systolic heart failure, diastolic heart failure, right-sided heart failure, left-sided heart failure, forward heart failure, backward heart failure, and high-output heart failure.

\* \* \* \* \*